United States Patent [19]
Wilson et al.

[11] Patent Number: 6,153,188
[45] Date of Patent: *Nov. 28, 2000

[54] GLYCOSYLATION VARIANTS OF IDURONATE 2-SULFATASE

[75] Inventors: Peter J. Wilson, North Adelaide; Charles Phillip Morris, Plympton; Donald Stewart Anson, Thebarton; Teresa Occhiodoro, Prospect; Julie Bielicki, Burnside; Peter Roy Clements, West Lakes; John Joseph Hopwood, Stonyfall, all of Australia

[73] Assignee: Women's and Children's Hospital, Australia

[*] Notice: This patent is subject to a terminal disclaimer.

[21] Appl. No.: 09/249,003

[22] Filed: Feb. 12, 1999

Related U.S. Application Data

[63] Continuation of application No. 08/345,212, Nov. 28, 1994, Pat. No. 5,932,211, which is a continuation of application No. 07/991,973, Dec. 17, 1992, abandoned, which is a continuation-in-part of application No. 07/790,362, Nov. 12, 1991, abandoned.

[51] Int. Cl.[7] .............................. A61K 38/46; C12N 9/16
[52] U.S. Cl. ........................................... 424/94.6; 435/196
[58] Field of Search ........................... 435/196; 424/94.6

[56] References Cited

PUBLICATIONS

Gottesman (1987) *Meth. Enzymol.* 151:3–8.
Peters, et al. (1990) "Phylogenetic Conservation of Arylsulfatases." *J. Biol. Chem.* 265(6):3374–3381.
Yen, et al. (1988) "The Human X–Linked Steroid Sulfatase Gene a Y–Encoded Pseudogene: Evidence for an Inversion of the Y Chromosome during Primate Evolution." *Cell* 55:1123–1135.
Robertson, et al. (1988) "Human Glucosamine–6–sulfatase cDNA Reveals Homology with Steroid Sulfatase." *Biochem. Biophys. Res. Commun.* 157 (1):218–224.
Yen, et al. (1987) "Cloning and Expression of Steroid Sulfatase cDNA and the Frequent Occurrence of Deletions in STS Deficiency: Implications for X–Y Interchange." *Cell* 49:443–454.
Stein, et al. (1989) "Cloning and Expression of Human Steroid–sulfatase." *J. Biol. Chem.* 264 (23):13865–13872.
Sasaki, et al. (1988) "cDNA cloning, nucleotide sequence and expression of the gene for arylsulfatase in the sea urchin (*Hemicentrous pulcherrimus*) embryo." *Eur. J. Biochem.* 177:9–13.
Anson, et al. (1992) "Correction of human mucopolysaccharidosis type VI fibroblasts with recombinant N–acetylgalactosamine–4–sulphatase." *Biochem. J.* 284:289–794.
Darnell, et al. (1986) *Molecular Cell Biology*, Scientific American Books, New York, NY:957–964.
Ferrara, et al. (1987) *FEBS Letters* 226:47–52.
Kodama, et al. (1992) *Glycobiology* 2:419–427.
Wilson, et al. (1990) "Hunter Syndrome: Isolation of an Iduronate–2–Sulfatase cDNA and Analysis of Patient DNA." *Proc. Natl. Acad. Sci. USA* 87:8531–8535.
Bielicki, et al. (1993) "Recombinant Human Iduronate–2–Sulphatase: Correction of Mucopolysaccharidosis—Type II Fibroblasts and Characterization of The Purified Enzyme." *Biochem. J.* 289:241–246.
Bielicki, et al. (1990) "Human liver iduronate –2–sulphatase." *Biochem J.* 271:75–86.
Stein, et al. (1989) "Cloning and Expression of Human Arylsulfatase A." *J. Biol. Chem.* 264 (2):1252–1259.

*Primary Examiner*—Rebecca E. Prouty
*Assistant Examiner*—M. Monshipouri
*Attorney, Agent, or Firm*—Ann R. Pokalsky

[57] ABSTRACT

The present invention provides a highly glycosylated iduronate-2-sulfatase enzyme comprising an iduronate-2-sulfatase polypeptide with at least 5 kilodalton (kDa) more sugar than iduronate-2-sulfatase purified from a natural source, e.g. human liver. The present invention also provides an enzymatically active polypeptide fragment or variant of such a highly glycosylated iduronate-2-sulfatase. The present invention further provides an isolated nucleic acid encoding iduronate-2-sulfatase, as well as an expression vector, a host cell and a method for producing the present highly glycosylated iduronate-2-sulfatase enzyme. In one embodiment the present invention is directed to a method for producing a glycosylated iduronate-2-sulfatase enzyme which comprises culturing a host cell containing a nucleic acid encoding an enzymatically active iduronate-2-sulfatase polypeptide wherein the host cell glycosylates the polypeptide to a greater degree than a native iduronate-2-sulfatase polypeptide expressed by a natural human liver cell.

19 Claims, 25 Drawing Sheets

CGGCTGTGTTGCGCAGTCTTCATGGGTTCCCGACGAGGAGGTCTCTGTGGCTGCGGCGGC 60
TGCTAACTGCGCCACCTGCTGCAGCCTGTCCCCGCTCTGAAGCGGCCGCGTCGAAGC 120

M  P  P  P  R  T  G  R  G  L  L  L  W  L  G  L  V  L  S  S    19
CGAAATGCCGCCCCCGACCGGACCGGGCCTTCTCTGGCCTTCTCTGGGTCTCTGGTTCTGAGCTC 180
                                                    *
V  C  V  A↓L  G↓S  E  T  Q  A  N  S  T  T  D  A  L  N  V    39
CGTCTGCGTGCCGCTCTGGGATCCGAAACGCAGGCCAACTCGACCACCAGATGCTCTGAACGT 240

L  L  I  V  D  D  L  R  P  S  L  G  C  Y  G  D  K  L  V    59
TCTTCTCATCATCGTGGATGACCTGCGCCCCTCCCTGGGCTGTTATGGGGATAAGCTGGT 320

```
R  S  P  N  I  D  Q  L  A  S  H  S  L  L  F  Q  N  A  F  A   79
GAGGTCCCCAAATATTGACCAACTGGCATCCCACAGCCTCTTCCAGAATGCCTTTGC    360

Q  Q  A  V  C  A  P  S  R  V  S  F  L  T  G  R  R  P  D  T   99
GCAGCAAGCAGTGTGCGCCCCGAGCCGCGTTCTTCCTCACTGGCAGGAGACCTGACAC   420
                                    *

T  R  L  Y  D  F  N  S  Y  W  R  V  H  A  G  N  F  S  T  I  119
CACCCGCCTGTACGACTTCAACTCCTACTGGAGGGTGCACGCTGGAAACTTCTCCACCAT 480

P  Q  Y  F  K  E  N  G  Y  V  T  M  S  V  G  K  V  F  H  P  139
CCCCCAGTACTTCAAGGAGAATGGCTATGTGACCATGTCGGTGGGAAAAGTCTTTCACCC 540
```

Figure 1B

```
            *
      G  I  S  S  N  H  T  D  D  S  P  Y  S  W  S  F  P  P  Y  H    159
      TGGGATATCTTCTAACCATACCGATGATTCTCCGTATAGCTGGTCTTTTCCACCTTATCA   600

P  S  S  E  K  Y  E  N  T  K  T  C  R  G  P  D  G  E  L  H    179
      TCCTTCCTCTGAGAAGTATGAAAACACTAAGACATGTCGAGGGCCAGATGGAGAACTCCA   660

A  W  L  L  C  P  V  D  V  L  D  V  P  E  G  T  L  P  D  K    199
      TGCCAACCTGCTTTGCCCCTGTGGATGTGCTGGATGTTCCCGAGGGCACCTTGCCTGACAA   720

Q  S  T  E  Q  A  I  Q  L  L  E  K  M  K  T  S  A  S  P  F    219
      ACAGAGCACTGAGCAAGCCATACAGTTGTTGGAAAAGATGAAAACGTCAGCCAGTCCTTT   780
```

Figure 1C

```
         F  L  A  V  G  Y  H  K  P  H  I  P  F  F  R  Y  P  K  E  F  Q    239
    CTTCCTGGCCGTTGGGTATCATAAGCCACACATCCCCTTCAGATACCCCAAGGAATTTCA           840
                                    *

K  L  Y  P  L  E  N  I  T  L  A  P  D  P  E  V  P  D  G  L       259
    GAAGTTGTATCCCTTGGAGAACATCACCCTGGCCCCCGATCCCGAGGTCCCTGATGGCCT           900

P  P  V  A  Y  N  P  W  M  D  I  R  Q  R  E  D  V  Q  A  L       279
    ACCCCCTGTGGCCTACAACCCCTGGATGGACATCAGGCAACGGGAAGACGTCCAAGCCTT           960
         *

N  I  S  V  P  Y  G  P  I  P  V  D  F  Q  R  K  I  R  Q  S       299
    AAACATCAGTGTGCCGTATGGTCCAATTCCTGTGGACTTTCAGCGGAAAATCCGCCAGAG          1020
```

Figure 1D

```
Y  F  A  S  V  S  Y  L  D  T  Q  V  G  R  L  L  S  A  L  D        319
CTACTTTGCCTCTGTGTCATATTTGGATACACAGGTCGGCCGCCTCTTGAGTGCTTTGGA     1080
                        *
D  L  Q  L  A  N  S  T  I  I  A  F  T  S  D  H  G  W  A  L        339
CGATCTTCAGCTGGCCAACAGCACCATCATTGCATTTACCTCGGATCATGGGTGGGCTCT     1140

G  E  H  G  E  W  A  K  Y  S  N  F  D  V  A  T  H  V  P  L        359
AGGTGAACATGGAGAATGGGCCAAATACAGCAATTTGATGTTGCTACCCATGTTCCCCT      1200

I  F  Y  V  P  G  R  T  A  S  L  P  E  A  G  E  K  L  F  P        379
GATATTCTATGTTCCTGGAAGGACGGCTTCACTTCCGGAGGCAGGGCGAGAAGCTTTTCCC   1260
```

Figure 1E

```
                Y  L  D  P  F  D  S  A  S  Q  L  M  E  P  G  R  Q  S  M  D   399
           TTACCTCGACCCTTTGATTCCGCCTCACAGTTGATGGAGCCAGGCAGGCAATCCATGGA        1320

L  V  E  L  V  S  L  F  P  T  L  A  G  L  A  G  L  Q  V  P   419
           CCTTGTGGAACTTGTGTCTCTTTTCCCACGCTGGCTGGACTTGCAGGACTGCAGGTTCC        1380

P  R  C  P  V  P  S  F  H  V  E  L  C  R  E  G  K  N  L  L   439
           ACCTCGCTGCCCCGTTCCTTCATTTCACGTTGAGCTGTGCAGAGAAGGCAAGAACCTTCT        1440

K  H  F  R  F  R  D  L  E  E  D  P  Y  L  P  G  N  P  R  E   459
           GAAGCATTTTCGATTCCGTGACTTGGAAGAGGATCCGTACCTCCCTGGTAATCCCCGTGA       1500
```

Figure 1F

```
       L  I  A  Y  S  Q  Y  P  R  P  S  D  I  P  Q  W  N  S  D  K    479
      ACTGATTGCCTATAGCCAGTATCCCGGCCTTCAGACATCCCTCAGTGGAATTCTGACAA    1560

P  S  L  K  D  I  K  I  M  G  Y  S  I  R  T  I  D  Y  R  Y    499
                                              *
      GCCGAGTTTAAAAGATATAAAGATCATGGGCTATTCCATACGCACCATAGACTATAGGTA    1620

T  V  W  V  G  F  N  P  D  E  F  L  A  N  F  S  D  I  H  A    519
      TACTGTGTGGGTTGGCTTCAATCCTGATGAATTTCTAGCTAACTTTTCTGACATCCATGC    1680

G  E  L  Y  F  V  D  S  D  P  L  Q  D  H  N  M  Y  N  D  S    539
                                                    *
      AGGGGAACTGTATTTTGTGGATTCTGACCCATTGCAGGATCACAATATGTATAATGATTC    1740
```

CCAAGGTGGAGATCTTTCCAGTGTTGATGCCTTGAGTTTGCCAACCATGGATGGCAA    1800

ATGTGATGTGCTCCCTTCCAGCTGGTGAGGAGGAGTTAGAGCTGGTCGTTTGTGATT    1860

ACCCATAATATTGGAAGCAGCCTGAGGGCTAGTTAATCCAAACATGCATCAACAATTGG  1920

CCTGAGAATATGTAACAGCCAAACCTTTCGTTTAGTCTTTATTAAATTTATAATTGGT   1980

AATTGGACCAGTTTTTTTAATTCCCTCTTTTAAAACAGTTACGGCTTATTTACTG      2040

AATAAATACAAAGCAAACATAACATTATACACAAAGAATACTTTCATTATTGTGGAATTAGTGC 2100
=====

TAATAACCAAACATAACATTATACACAAAGAATACTTTCATTATTGTGGAATTAGTGC   2160

ATTTCAAAAGTAATCATATATCAAACTAGGCACCACACTAGTTCCTGATTATTTGTT    2220

TATAATTTAATAATATATCTTATGAGCCCTATATATTCAAAATATTATGTTAACATGTAA 2280

TCCATGTTTCTTTTTCC                                           2297
```

```
2    MPPPRTGRGLLIWLGLIVLSSVCVALGSETQANST

6    MGAPRSLLLALAAGLAVA

A    MGPRGAASLPRGPGPRRLLLPVVLPLLLLLLLAPPGSGA

B    MPLRKMKIPFLLLFFLWEAES

C    MKSAPFLFLLGLLGLVTAQTQDPALLDLLRENPDLLSLLLQSNEHR

2    TDALNVLLIIVDDLR-PSLGCYGDKLIVRSPNIDQLASHSLLFQNAFAQQAVCAPSRVSFLTGR

6    TRRPNVVLLLTDDQD-EVLGGMTPLKKTKALIGEM---GMTFSSAYVPSALCCPSRASILTGK

A    RPPNIVLIFADDLGYGDLGCYGHPSSTTPNLDQLAAGGLRFTDFYVPVSLCTPSRAALLTGR

B    GASRPPHLVFLLADDLGWNDVG-FHGSRIRTPHLDALAAGGVLLDNYYTQ-PLCTPSRSQLLTGR

C    HAASRPNIILVMADDLGIGDPGCYGNKTIRTPNIDRLASGGVKLTQHLAASPLCTPSRAAFMTGR

U    APLVKPNVVLLVADDMGSGDLTSYGHPTQEAGFIDKMAAEGLRFTNGYVGDAVCTPSRSAIMTGR

2   RPDTTRLYD------FN-----SYWRVHAGNFSTIPQYFKEN-GYVIMSVGK-VFHPGISSNHT
6   YPHNHHVVN----NTLEGNCSSKSWQKIQEPNTFPAILRSMGGYQIFFAGK-YLNEYGAPDA
A   LPVRMGMYP------GVLV---PSSRGGLPLEEVTVAEVLAAR-GYLIGMAGK-WHLGVG----
B   YQIRTGLQH------QIIW---PCQPSCVPLDEKLLPQLLKEA-GYTTHMVGK-WHLGMY----
C   YPVRSGMASWSRTGVFL--FTASSGGLPTDEITFAKLLKDQ-GYSTALIGK-WHLGMSCHSK
U   LPVRIGTFG--ETRVFL---PWTKTGLPKSELTIAEAMKEA-GYATGMVGK-WHLGMNENSS
                *           *                ** *   ** ****

2   DDSP-------YSWSFPPYHPS-SEKYENTKTCRGPDGE----------LHA
6   GGLEHVPL--GWSYWYALEKNS--KYYNYTLSINGKARK---------H
A   PEGAFLPPHQGFHRFLGIPYSH-DQGPCQNLTCFPPATP---------C
B   RKEC-LPTRRGFDTYFGYLLGS-EDYYSHERCTLIDAL----------N
C   TDFCHHPLHHGFNYFYGISLTNLRDCKPGEGSVFTTGFKRLVFLPLQIVGVTLLTLA
U   TDGAHLPFNHGFD-FVGHNLPF-TNSWSCDDTGLHKDFP---------D
           *   **               *

```
B ─────────────────────────────────────────────────────────────────────────────
2   NLLCPVDVLDVPEGTLPDKQSTEQAIQLLEKMKTSASPFFLAVGYHKPHIPFRYPKEFQKLY
6   GENYSVDYLTDVLA----------------------------NVSLDF------LDYKSNFEPFF
A   DGGCDQGLVPIPL-----------------------------------------------------
B   VTRC-----ALD------------------------------------------------------
C   ALNC-LGLLHVPLG----------------------VFFSLLFLAALILTLFLGF------LHYFRPLNCF-
U   SQRC------YL------------------------------------------------------
               *

2   -----PLENITLAPDPEVPDGLPPVAYNPWMDIRQR--EDVQALNISVPYGPIPVDF
6   MMIATPAPHSPWTAAPQYQKAFQNVFAPRNKNFNIH--GTNKHWLI----RQAKTPM
A   ------LANLSVEAQPPWLPGLEARYMAFAHDLMADAQRQDRPFFLYYASHHTHYPQ
B   ------FRDGEEVATGYKNMYSTNIFTKRAIALITN-HPPEKPLFLYLALQSVHEPL
C   ------MMRNYEIIQQPMSYDNLTQRLTVEAAQFIQ--RNTETPFLLVLSYLHVHTAL
U   ------YVNATLVSQPYQHKGLTQLFTDDALGFIED--NHADPFFLYVAFAHMHTSL
            *                                *    *    *    *
```

Figure 3C

```
2  ----------QRKIRQSYFASVSYLDTQVGRLLSALDDLQLANSTIIAFTSDHGWALGE
6  TN------SSIQFLDNAFRKRW-QTLLSVDDLVEKLVKRLEFTGELNNTYIFYTSDNGYHTG-
A  ------FSGQSFAERSGRGPFGDSLMELDAAVGTLMTAIGDLGLLEETLVIFTADNGPETMR
B  QVPEEYLKPYDFIQDKNRHHYAGMVSLMDEAVGNVTAALKSSGLWNNTVFIFSTDNGGQTL-
C  ------FSSKDFAGKSQHGVYGDAVEEMDWSVGQILNLLDELRLANDTLIYFTSDQAHVEE
U  ------FSSDDFSCTSRRGRYGDNLLEMHDAVQKIVDKLEENNISENTIFFISDHGPHREY
             *                                        *    *   *

2  HGEWAKYSNFDVATHVPLIFYVPGRTASLPEAGEKLFPYLDPFDSASQLMEPGRQSM
6  ------------QFSL-----PIDKRQLYEFDIKV----PLLVRGPGIK-PNQTSK
A  MS----------RCGKGTTYEGGVRE----PALAFWPGHIAPGVT-H
B  ------------RGRKWSLWEGGVRG----VGFVASPLLKQKGVKNR
C  VSSKGEI-----KGGKANNWEGGIRV----PGILRWPRVIQAGQKID
U  CE----------RGGKSHSWEGGHRI----PYIVYWPGTISPGIS-N
**    *             ***          *
```

Figure 3D

```
2   DLVELVSLFPTLAGLAGLQVPPRCPVPSFHVELCREGKNLLKHFRFRDLEEDPYLPGNPREL
6   MLVANIDLGPTILDIAGYDLNKT-QMDGMSL------------LPILRGASNLTWRSDVL
A   ELASSLDLLPTLAALAGAPLPNV-TLDGFDL------------RPPAAGHRQEPSAVSLL
B   ELIHISDWLPTLVKLARGHTNGTKPLDGFDV------------WKTISEGSPSP-RIELL
C   EPTSNMDIFPTVAKLAGAPLPEDRIIDGRDL------------MPLLEGKSQRSDHEFLF
U   EIVTSMDIIATAADLGGTTLPTDRIYDGKSI------------KDVLLEGSASP-HSSFF
     *       *   *              **

2   IAYSQYPRPSDIPQWNSDKPSLKDIKIMGYSIRTIDYRYTVWVG-------------
6   VEYQGEGRNVTDPTCPSLSPGVSQCFPDCVCEDAYNNTYACVRTMSALW-NLQYC---
A   LPVLPRRGPWGFCCAD----WKVQGSLLHPGSAHSDTTAD--------------PAC--
B   HNIDPNFVDSSPCPRNSMAPAKDDSSLPEYSAFNTSVHAAIRHGNWKLLTGYPGCGY
C   HYCNAYLNAVRWHPQNSTSIWKAFFFTPNFNPVGSNGCFAT--------------HVC--
U   YYCKDNLMAVRGKYKAHFRTQRVRSQDEYGLECAGG-FPL--------------EDY--
```

Figure 3E

```
2  -FNPDE---FLANFSDIHAGE-----LYFVDSDFLQDHNMY---NDSQGGDLFQLLMP
6  ------------EFDDQEVFVEVYNLTADPDQITNI---AKTIDPELLGKMNYRLMMLQS
A  ---------HASSSLTAHEPP---L-LYDLSKDPGENYNLLGGVAGATPEVLQALKQLQLLKAQ
B  WFPPPSQYNVSEIPSSDPPTKTLWLFDIDRDPEERHDL----SREYPHIVTKLLSRLQFYHKH
C  -F------CFGSYVTHHDPP---L-LFDISKDPRERNPL---TPASEPRFYEILKVMQEAADR
U  -FDCND-CEGDCVTEHDPP----L-LFDLHRDPGEAYPL--EACGHEDVFLTVKSTVEEHKAA
         **      *          *  *   **  *       *

2  CSGPTCRTPGVFDPGYR-FDPRLMF-------SNRGSVRTRRFSKHLL
6  LDAAVTFGPSQVARGE---DPALQICCHPGCTPRPACCHCPDPHA
A  SVPV--YFPAQ--------DPR-----CD-----PKATGVWGPWM
B  HTQTLPEVPDQFSWNNFLWKPWLQLCCP-----STGLSCQCDREKQDKRLSR
C  LVKGTPLLDSFDHSIVPCCNPANGCICNYVHEPGMPECYQDQVATAARHYRP
U        *
```

Figure 3F gcgatctagacctagttagccaagtctctaacgtgacataggaagcttgcaatggcaactggccgc ccgtctgcgcctgtctctcgccacgcctattgtgcaggatgacgcacctctatgaacccgccgtg aggtgagtgtgacgcaggaagagtcgcacgacgactcgCgtgccgcagtgcgggccgggcccggg cggcggctgtgttgcgcagtcttcatgggtccccgcctgcccgcgctctgaagccgcgtggctgcta actgcgccacctgctgcagcctgtcccgcgctctgaagccgcgtgaagccgaa..exonI..

ATGCCGCCACCCCGACCGGCCTTCTCTGGCTGCTCTGGTTCTGAGCTCCGTCTGGTCGC

CCTCGGATCCGAAACGCAGGCCAACTGACCACAGgtgccgccacgccctccttcctcctctctc ccttcctcctCtccctccttcctcctccttgtttatatccattctttttac c.intronI..ccccactcccacccttgctgaggcacagcgccctaccatgagggaggttcagtgtcagtgc agggtccagccttgggcctcttagtaacctagcacctaggctgttaggtgc
aggttcagtgtcagtgcagg

Figure 7A

A ttacctcaccaagcccctccctcctgtgtag......exonII...ATGCTCTGAACGTTCTCTCA
TCATCGTGGATGACCTGCGCCCCTGGCTGTTATGGGATAAGCTGGTGAGTCCCAAATATT
GACCAACTGGCATCCCACAGCCTCCTCTTCCAGAATGCCTTTGCGCAGtatgtctgggaacctctag
ctgtgggtgtgtgctcgtgcactgagggtgggggcggggagcttcagtcagtattgtcagatggca
cagattgtgcgggacatcttgttagagggaagcatagtctggaaa..intron2..agggcggttgct
tggttacctaagagatggcagacatgttttgctgtggcgatgcttacctctgctccctaaca
g......exonIII..CAAGCAGTGTGCCCCGAGCCGCGTTCTTCCTCACTGGCAGGAGACCTG
ACACCACCCGCCTGTACGACTTCAACTCCTACTGGAGGGTGCACGCTGGAAACTTCCACCATCCCC
CAGTACTTCAAGGAGAATGGCTATGTGACCATGTCGGTGGGAAAAGTCTTTCACCCTGgtactgctcc
atgtccagagtctgggttctcttggtgtctgantccagcattcccatcctgggatgggct

B gtctttgcagagccctctctggctgggcgagtccctcgctagtcagtgct..intron3..tttgta
gatgaggaaactgagcccaaagaaggaggntccacttgccattgttacagagtttaattatg
gggagtggggtgttgaaagactcatcatgttttaacaaccttttttttttccaag......exonIV
..GGATATCTTCTAACCATACCGATGATTCTCCGTATAGCTGGTCTTTTCCACCTTATCATCCTTCCT
CTGAGAAGTATGAAAAACACTAAGgtaaggctgtgaagctgtcatgtnctgtgaagctggtatataccacgaagttgtggg
tttgtcacataaactactgggtatactgaagtaagt......intron4..tgttcagtctgagtgacta
tttcatttgtgataatgttttgacagaagtaagt..tgttcagtctgagtgacta
acacgtgaagggctgattatgtgaacattaaatctgtgtgtagccttcatgctcatntccttgca
cttaaaaagctgatgtttatattattttgttttgaaag..exonV..ACATGTCGAGGGCCAGATGGAG
AACTCCATGCCAACCTGCTTTGCCCTGTGGCTGGATGTTCCCGAGGGCACCTTGCCTGACAAA

CAGAGCACTGAGAGCAAGCCATACAGTTGTTGAAAAGATGAAAAGTCAGCCAGTCCTTCTTCCTGGC
CGTTGGGTATCATAAGCCACACATCCCCTTCAGATACCCCAAGgtgaagagctgttgagggctgatc
cagcacagctgtgacagctgtgttgttgttgagggagggattcgcacaggaaggtggctacatcct
gccatcgccaggcaccatggttgcctgatgggcactagtgtcctcagtggagtaaagatgggattag
aggt.....intron5..aaaaggcagtatagacagtgatagagccacaagcttgtgcttttgctaaa
agagtgacaactttgtgctttgtgttttccccaag...exonVI...GAATTTCAGAAGTTGTATC
CCTTGGAGAACATCACCCTGGCCCCCGATCCCGAGGTCCCTACCCCTGTGGCCTACAAC
CCCTGGATGGACATCAGGCAACGGGAAGACGTCCAAGCCTTAAACATCAGTGTGCCGTATGGTCCAAT
TCCTGTGGACTTTCAGgtatcaaggacatagtttggggatgtattggacactgatgacatagtgtcgt
aggtgaaccactcttctcagtagacacaactccacctataatgtcttattaagagctttctttgtgt

Figure 7D g..intron6..tagggattgggagagatgcacacggcaagcattatctctgtatgcctggcaattt
aaattgcagtcactctcattttattttttcaattgcag.....exonVII..CGGAAAATCCGC
CAGAGCTACTTTGCCTCTGTGTCATATTTGGATACACAGGTCGGCCGCCTCTTGAGTGCTTTGGACGA
TCTTCAGCTGGCCAACAGCACCATCATTGCATTTACCTCGGATCATGgtaagcatttgaattccct
ggtgagtcaaaacatctgaactttcctgtgaaacatgctttgcaaaattgccattgacataaacatgg
gtgtg..intron7..tttcttctaggtgatgagttctactcctcggttttacaacaggaaatg
aaatggtatctaaataacaagctgtgtatgatgatattcattctcgtcattctgcttttta
tgaactag..exonVIII..GGTGGGCTCTAGGTGAACATGGAGAATGGGCCAAATACAGCAATTTGA
TGTTGCTACCATGTTCCCCTGATATTCTATGTTCCTGAAGGACGGCTTCACTTCCGGAGGCAGGCG
AGAAGCTTTTCCCTTACCTGACCCTTTGATTCCGCCTCACAGTTGATGGAGCCAGgtataaatat

Figure 7E gctgaaatgatattgcttgacagtaagatcacctttagtttatatgtgaaccacttattgaatcata
ggctttgggggttacacagaccccc...intron8..aaagataaatggtgtaattaaaaagaaaac
atatggagccagacagggtccttactgctcctgcctggcatggcaggctttataatgtaaccca
ttctgctctgtcgttcctgtttcag..exonIX..GCAGGCAATCCATGGACCTTGTGAACTTGTG
TCTCTTTTTCCCACGCTGGACTGCAGGACTGCAGGTTCCACCTGCTGCCCCGTTCCTTCATT
TCACGTTGAGCTGTGCAGAGAAGGCAAGAACCTTCTGAAGCATTTCGATTCCGTGACTGGAAGAGG
ATCCGTACCTCCCCTGGTAATCCCCGTGAACTGATTGCCTATAGCCAGTATCCCCGGCCTTCAGACATC
CCTCAGTGGAATTCTGACAAGCCGAGTTTAAAGATATAAAGATCATGGCTATTCCATACGCACCAT
AGACTATAGGTATACTGTGTGTGGGTTGGCTTCAATCCCTGATGAATTTCTAGCTAACTTTTCTGACATCC
ATGCAGGGGAACTGTATTTGTGGATTCTGACCCATTGCAGGATCACAATATGTATAATGATTCCCAA

Figure 7F

GGTGGAGATCTTTCCAGTTGTTGATGCCTTGAgttttgccaaccatggatggcaaatgtgatgtgct
cccttccagctggtgagaggaggagttagagctggtcgttttgtgattacccataatattggaagcag
cctgagggctagtgttaatccaaacatgcatcaacaattggcctgagaatatgtaacagccaacctt
tcgtttagtctttattaaaatttataattggtaattggaccagtttttttttaattccctctttt
aaaacagttacggcttattactgaataaatacaaagcaaacataacattatacacaaagaatactttcattatttgtggaa
atacgaagaccatacaataaccaaacataatcatatcaaactaggcaccacactagtcctgattatttgtt
tttagtgcatttcaaaagtaatcatatatcttatgagccctatattcaaatatattatgttaacatgtaatccatgtt
tataatttaatatatcttatgagccctatattcaaatatattatgttaacatgtaatccatgtt
tcttttttcc

Figure 7G

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
       (A) LENGTH: 2297 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: CDS
       (B) LOCATION: 125..1774

(xi) SEQUENCE DESCRIPTION: SEQ ID NO:1:

```
CGGCTGTGTT GCGCAGTCTT CATGGGTTCC CGACGAGGAG GTCTCTGTGG CTGCGGCGGC      60

TGCTAACTGC GCCACCTGCT GCAGCCTGTC CCCGCCGCTC TGAAGCGGCC GCGTCGAAGC     120

CGAA ATG CCG CCA CCC CGG ACC GGC CGA GGC CTT CTC TGG CTG GGT CTG     169
     Met Pro Pro Pro Arg Thr Gly Arg Gly Leu Leu Trp Leu Gly Leu
      1               5                  10                  15

GTT CTG AGC TCC GTC TGC GTC GCC CTC GGA TCC GAA ACG CAG GCC AAC     217
Val Leu Ser Ser Val Cys Val Ala Leu Gly Ser Glu Thr Gln Ala Asn
             20                  25                  30

TCG ACC ACA GAT GCT CTG AAC GTT CTT CTC ATC ATC GTG GAT GAC CTG     265
Ser Thr Thr Asp Ala Leu Asn Val Leu Leu Ile Ile Val Asp Asp Leu
         35                  40                  45

CGC CCC TCC CTG GGC TGT TAT GGG GAT AAG CTG GTG AGG TCC CCA AAT     313
Arg Pro Ser Leu Gly Cys Tyr Gly Asp Lys Leu Val Arg Ser Pro Asn
     50                  55                  60

ATT GAC CAA CTG GCA TCC CAC AGC CTC CTC TTC CAG AAT GCC TTT GCG     361
Ile Asp Gln Leu Ala Ser His Ser Leu Leu Phe Gln Asn Ala Phe Ala
 65                  70                  75

CAG CAA GCA GTG TGC GCC CCG AGC CGC GTT TCT TTC CTC ACT GGC AGG     409
Gln Gln Ala Val Cys Ala Pro Ser Arg Val Ser Phe Leu Thr Gly Arg
 80                  85                  90                  95

AGA CCT GAC ACC ACC CGC CTG TAC GAC TTC AAC TCC TAC TGG AGG GTG     457
Arg Pro Asp Thr Thr Arg Leu Tyr Asp Phe Asn Ser Tyr Trp Arg Val
                 100                 105                 110

CAC GCT GGA AAC TTC TCC ACC ATC CCC CAG TAC TTC AAG GAG AAT GGC     505
His Ala Gly Asn Phe Ser Thr Ile Pro Gln Tyr Phe Lys Glu Asn Gly
             115                 120                 125

TAT GTG ACC ATG TCG GTG GGA AAA GTC TTT CAC CCT GGG ATA TCT TCT     553
Tyr Val Thr Met Ser Val Gly Lys Val Phe His Pro Gly Ile Ser Ser
         130                 135                 140

AAC CAT ACC GAT GAT TCT CCG TAT AGC TGG TCT TTT CCA CCT TAT CAT     601
Asn His Thr Asp Asp Ser Pro Tyr Ser Trp Ser Phe Pro Pro Tyr His
     145                 150                 155

CCT TCC TCT GAG AAG TAT GAA AAC ACT AAG ACA TGT CGA GGG CCA GAT     649
Pro Ser Ser Glu Lys Tyr Glu Asn Thr Lys Thr Cys Arg Gly Pro Asp
160                 165                 170                 175

GGA GAA CTC CAT GCC AAC CTG CTT TGC CCT GTG GAT GTG CTG GAT GTT     697
Gly Glu Leu His Ala Asn Leu Leu Cys Pro Val Asp Val Leu Asp Val
                 180                 185                 190

CCC GAG GGC ACC TTG CCT GAC AAA CAG AGC ACT GAG CAA GCC ATA CAG     745
Pro Glu Gly Thr Leu Pro Asp Lys Gln Ser Thr Glu Gln Ala Ile Gln
             195                 200                 205
```

```
TTG TTG GAA AAG ATG AAA ACG TCA GCC AGT CCT TTC TTC CTG GCC GTT      793
Leu Leu Glu Lys Met Lys Thr Ser Ala Ser Pro Phe Phe Leu Ala Val
            210                 215                 220

GGG TAT CAT AAG CCA CAC ATC CCC TTC AGA TAC CCC AAG GAA TTT CAG      841
Gly Tyr His Lys Pro His Ile Pro Phe Arg Tyr Pro Lys Glu Phe Gln
            225                 230                 235

AAG TTG TAT CCC TTG GAG AAC ATC ACC CTG GCC CCC GAT CCC GAG GTC      889
Lys Leu Tyr Pro Leu Glu Asn Ile Thr Leu Ala Pro Asp Pro Glu Val
240                 245                 250                 255

CCT GAT GGC CTA CCC CCT GTG GCC TAC AAC CCC TGG ATG GAC ATC AGG      937
Pro Asp Gly Leu Pro Pro Val Ala Tyr Asn Pro Trp Met Asp Ile Arg
            260                 265                 270

CAA CGG GAA GAC GTC CAA GCC TTA AAC ATC AGT GTG CCG TAT GGT CCA      985
Gln Arg Glu Asp Val Gln Ala Leu Asn Ile Ser Val Pro Tyr Gly Pro
            275                 280                 285

ATT CCT GTG GAC TTT CAG CGG AAA ATC CGC CAG AGC TAC TTT GCC TCT     1033
Ile Pro Val Asp Phe Gln Arg Lys Ile Arg Gln Ser Tyr Phe Ala Ser
            290                 295                 300

GTG TCA TAT TTG GAT ACA CAG GTC GGC CGC CTC TTG AGT GCT TTG GAC     1081
Val Ser Tyr Leu Asp Thr Gln Val Gly Arg Leu Leu Ser Ala Leu Asp
305                 310                 315

GAT CTT CAG CTG GCC AAC AGC ACC ATC ATT GCA TTT ACC TCG GAT CAT     1129
Asp Leu Gln Leu Ala Asn Ser Thr Ile Ile Ala Phe Thr Ser Asp His
320                 325                 330                 335

GGG TGG GCT CTA GGT GAA CAT GGA GAA TGG GCC AAA TAC AGC AAT TTT     1177
Gly Trp Ala Leu Gly Glu His Gly Glu Trp Ala Lys Tyr Ser Asn Phe
            340                 345                 350

GAT GTT GCT ACC CAT GTT CCC CTG ATA TTC TAT GTT CCT GGA AGG ACG     1225
Asp Val Ala Thr His Val Pro Leu Ile Phe Tyr Val Pro Gly Arg Thr
            355                 360                 365

GCT TCA CTT CCG GAG GCA GGC GAG AAG CTT TTC CCT TAC CTC GAC CCT     1273
Ala Ser Leu Pro Glu Ala Gly Glu Lys Leu Phe Pro Tyr Leu Asp Pro
            370                 375                 380

TTT GAT TCC GCC TCA CAG TTG ATG GAG CCA GGC AGG CAA TCC ATG GAC     1321
Phe Asp Ser Ala Ser Gln Leu Met Glu Pro Gly Arg Gln Ser Met Asp
385                 390                 395

CTT GTG GAA CTT GTG TCT CTT TTT CCC ACG CTG GCT GGA CTT GCA GGA     1369
Leu Val Glu Leu Val Ser Leu Phe Pro Thr Leu Ala Gly Leu Ala Gly
400                 405                 410                 415

CTG CAG GTT CCA CCT CGC TGC CCC GTT CCT TCA TTT CAC GTT GAG CTG     1417
Leu Gln Val Pro Pro Arg Cys Pro Val Pro Ser Phe His Val Glu Leu
            420                 425                 430

TGC AGA GAA GGC AAG AAC CTT CTG AAG CAT TTT CGA TTC CGT GAC TTG     1465
Cys Arg Glu Gly Lys Asn Leu Leu Lys His Phe Arg Phe Arg Asp Leu
            435                 440                 445

GAA GAG GAT CCG TAC CTC CCT GGT AAT CCC CGT GAA CTG ATT GCC TAT     1513
Glu Glu Asp Pro Tyr Leu Pro Gly Asn Pro Arg Glu Leu Ile Ala Tyr
            450                 455                 460

AGC CAG TAT CCC CGG CCT TCA GAC ATC CCT CAG TGG AAT TCT GAC AAG     1561
Ser Gln Tyr Pro Arg Pro Ser Asp Ile Pro Gln Trp Asn Ser Asp Lys
            465                 470                 475

CCG AGT TTA AAA GAT ATA AAG ATC ATG GGC TAT TCC ATA CGC ACC ATA     1609
Pro Ser Leu Lys Asp Ile Lys Ile Met Gly Tyr Ser Ile Arg Thr Ile
480                 485                 490                 495

GAC TAT AGG TAT ACT GTG TGG GTT GGC TTC AAT CCT GAT GAA TTT CTA     1657
Asp Tyr Arg Tyr Thr Val Trp Val Gly Phe Asn Pro Asp Glu Phe Leu
            500                 505                 510

GCT AAC TTT TCT GAC ATC CAT GCA GGG GAA CTG TAT TTT GTG GAT TCT     1705
Ala Asn Phe Ser Asp Ile His Ala Gly Glu Leu Tyr Phe Val Asp Ser
```

```
                 515                 520                 525
GAC CCA TTG CAG GAT CAC AAT ATG TAT AAT GAT TCC CAA GGT GGA GAT    1753
Asp Pro Leu Gln Asp His Asn Met Tyr Asn Asp Ser Gln Gly Gly Asp
        530                 535                 540

CTT TTC CAG TTG TTG ATG CCT TGAGTTTTGC CAACCATGGA TGGCAAATGT       1804
Leu Phe Gln Leu Leu Met Pro
545                 550

GATGTGCTCC CTTCCAGCTG GTGAGAGGAG GAGTTAGAGC TGGTCGTTTT GTGATTACCC  1864

ATAATATTGG AAGCAGCCTG AGGGCTAGTT AATCCAAACA TGCATCAACA ATTTGGCCTG  1924

AGAATATGTA ACAGCCAAAC CTTTTCGTTT AGTCTTTATT AAAATTTATA ATTGGTAATT  1984

GGACCAGTTT TTTTTTTAAT TTCCCTCTTT TTAAAACAGT TACGGCTTAT TTACTGAATA  2044

AATACAAAGC AAACAAACTC AAGTTATGTC ATACCTTTGG ATACGAAGAC CATACATAAT  2104

AACCAAACAT AACATTATAC ACAAAGAATA CTTTCATTAT TTGTGGAATT TAGTGCATTT  2164

CAAAAAGTAA TCATATATCA AACTAGGCAC CACACTAAGT TCCTGATTAT TTTGTTTATA  2224

ATTTAATAAT ATATCTTATG AGCCCTATAT ATTCAAAATA TTATGTTAAC ATGTAATCCA  2284

TGTTTCTTTT TCC                                                    2297
```

(2) INFORMATION FOR SEQ ID NO:2:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Pro Pro Arg Thr Gly Arg Gly Leu Leu Trp Leu Gly Leu Val
 1               5                  10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205
```

```
Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
                260                 265                 270

Arg Glu Asp Val Gln Ala Leu Asn Ile Ser Val Pro Tyr Gly Pro Ile
                275                 280                 285

Pro Val Asp Phe Gln Arg Lys Ile Arg Gln Ser Tyr Phe Ala Ser Val
                290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Trp Ala Lys Tyr Ser Asn Phe Asp
                340                 345                 350

Val Ala Thr His Val Pro Leu Ile Phe Tyr Val Pro Gly Arg Thr Ala
                355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
                420                 425                 430

Arg Glu Gly Lys Asn Leu Leu Lys His Phe Arg Phe Arg Asp Leu Glu
                435                 440                 445

Glu Asp Pro Tyr Leu Pro Gly Asn Pro Arg Glu Leu Ile Ala Tyr Ser
                450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
                515                 520                 525

Pro Leu Gln Asp His Asn Met Tyr Asn Asp Ser Gln Gly Gly Asp Leu
                530                 535                 540

Phe Gln Leu Leu Met Pro
545                 550

(2) INFORMATION FOR SEQ ID NO:3:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:
```

```
Pro Arg Glu Leu Ile Ala Tyr Ser Asn Tyr Pro Arg Asn Asn Ile Pro
1               5                   10                  15
```

(2) INFORMATION FOR SEQ ID NO:4:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
ACTAGTAGCA CCTGCTGGAC GCCGGGAGGG ACCCGCTGAT GCTGCTGCA            49
```

(2) INFORMATION FOR SEQ ID NO:5:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Thr Ser Ala Leu Asn Val Leu Leu Ile Ile Val Asp Asp Leu Arg Pro
1               5                   10                  15

Ser Leu Gly Asp Tyr Asp Asp Val Leu
            20                  25
```

(2) INFORMATION FOR SEQ ID NO:6:

(i) SEQUENCE CHARACTERISTICS:
        (A) LENGTH: 4428 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 332..434

(ix) FEATURE:
        (A) NAME/KEY: intron
        (B) LOCATION: 536..537

(ix) FEATURE:
        (A) NAME/KEY: CDS
        (B) LOCATION: 693..829

(ix) FEATURE:
        (A) NAME/KEY: intron
        (B) LOCATION: 962..963

(ix) FEATURE:
        (A) NAME/KEY: CDS
        (B) LOCATION: 1044..1221

(ix) FEATURE:
        (A) NAME/KEY: intron
        (B) LOCATION: 1350..1351

(ix) FEATURE:
        (A) NAME/KEY: CDS
        (B) LOCATION: 1480..1569

(ix) FEATURE:
        (A) NAME/KEY: intron
        (B) LOCATION: 1716..1717

```
         (ix) FEATURE:
              (A) NAME/KEY: CDS
              (B) LOCATION: 1841..2041

(ix) FEATURE:
              (A) NAME/KEY: intron
              (B) LOCATION: 2206..2207

(ix) FEATURE:
              (A) NAME/KEY: CDS
              (B) LOCATION: 2294..2464

(ix) FEATURE:
              (A) NAME/KEY: intron
              (B) LOCATION: 2585..2586

(ix) FEATURE:
              (A) NAME/KEY: CDS
              (B) LOCATION: 2684..2810

(ix) FEATURE:
              (A) NAME/KEY: intron
              (B) LOCATION: 2904..2905

(ix) FEATURE:
              (A) NAME/KEY: CDS
              (B) LOCATION: 3033..3206

(ix) FEATURE:
              (A) NAME/KEY: intron
              (B) LOCATION: 3308..3309

(ix) FEATURE:
              (A) NAME/KEY: CDS
              (B) LOCATION: 3435..3908

(xi) SEQUENCE DESCRIPTION: SEQ ID NO:6:

GCGATCTAGA CCTAGTTAGC CAAGTCTCTA ACGTGACATA GGGAAAGCTT GCAATGGCAA      60

CTGGCCGCCC GTCTGCGCCT GTCTCTCGCC ACGCCTATTG CTGCAGGATG ACGCGCACCT     120

CTATGAACCC GCCGTGAGGT GTGAGTGTGA CGCAGGGAAG AGTCGCACGG ACGCACTCGC     180

GCTGCGGCCA GCTGCGGGCC CGGGCGGCGG CTGTGTTGCG CAGTCTTCAT GGGTTCCCGA     240

CGAGGAGGTC TCTGTGGCTG CGGCGGCTGC TAACTGCGCC ACCTGCTGCA GCCTGTCCCC     300

GCCGCTCTGA AGCGGCCGCG TCGAAGCCGA AATGCCGCCA CCCCGGACCG GCCGAGGCCT     360

TCTCTGGCTG GGTCTGGTTC TGAGCTCCGT CTGCGTCGCC CTCGGATCCG AAACGCAGGC     420

CAACTCGACC ACAGGTGCCG CCCACGCCCT CCCTGCCATC TCTTCTCCCT TCCTCCCTCC     480

CTTCCTTCCT CCTTCCTTCT TTCCTTCCTT CTTTGTTTAT ATCCATTCTT TTTACCCCCC     540

ACTCCCACCC TTGCTGAGGC ACAGCGCCCT CCCTGGCTAG GCTGTTAGGT GCAGGGTCCA     600

GCCTTGGGCC TCTTAGTAAC CTAGCACCTA CCATGAGGGA GGGTTCAGTG TCAGTGCAGG     660

TTACCTCACC AAAGCCCCTC CCTCCTGTGT AGATGCTCTG AACGTTCTTC TCATCATCGT     720

GGATGACCTG CGCCCCTCCC TGGGCTGTTA TGGGGATAAG CTGGTGAGGT CCCCAAATAT     780

TGACCAACTG GCATCCCACA GCCTCCTCTT CCAGAATGCC TTTGCGCAGG TATGTCTGGG     840

AACCTCTAGC TGTGGGTGTG TGCTGCTTCG TGCACTGAGG GTTGGGGCG GGGAGCTTCA      900

GCTATTGTCA GATGGCACAG ATTGTGCGGG ACATCTTGTT AGAGGGAAGC ATAGTCTGGA     960

AAAGGGCGGT TGCTTGGTTA CCTAAGAGAT GGCAGACATG TTTTGCTGTG GCGATGCTTA    1020

CCTCTGCTTC TGCTCCCTAA CAGCAAGCAG TGTGCGCCCC GAGCCGCGTT TCTTTCCTCA    1080

CTGGCAGGAG ACCTGACACC ACCCGCCTGT ACGACTTCAA CTCCTACTGG AGGGTGCACG    1140

CTGGAAACTT CTCCACCATC CCCCAGTACT TCAAGGAGAA TGGCTATGTG ACCATGTCGG    1200
```

```
TGGGAAAAGT CTTTCACCCT GGTACTGCTC CATGTCCAGA GTCTGGGTTC TCTTGGTTTG    1260

TGGTGTCTGA NTCCAGCATT CCCATCCTGG GGATGGGCTG TCTTTGCAGA GCCCTCTTCT    1320

GGCTGGGCGA GTCCCTCGCT AGTCAGTGCT TTTGTAGATG AGGAAACTGA GCCCCAAAGA    1380

AGGGAGGNTC CACTTGCCCA TTTGTTTACA GAGTTTTAAT TATGGGGAGT GGGGTGTTGA    1440

AAGACTCATC ATGTTTTAAC AACCTTTTTT TTTTTCCAAG GGATATCTTC TAACCATACC    1500

GATGATTCTC CGTATAGCTG GTCTTTTCCA CCTTATCATC CTTCCTCTGA GAAGTATGAA    1560

AACACTAAGG TAAGGCTGTG AAAGGGACAT TTCTGAAGAG GAACCACTTT TCCTTTGTC    1620

ACATAAACTA CTGGGTATAC TGCATGTNCT GTGAAGCTGG TTATATACCA CGAAGTTGTG    1680

GGTTTCATTT GTGATAATGT TTTGACAGAA GTAAGTTGTT CAGTCTGAGT GACTAACACG    1740

TGAAGGGCTG ATTATGTGAA CATTAAATCT GTGTGTGTAG CCTTCATGGC TTCATNTCTT    1800

GCACTTAAAA AGCTGATGTT ATATTATTTT GTTTTGAAAG ACATGTCGAG GGCCAGATGG    1860

AGAACTCCAT GCCAACCTGC TTTGCCCTGT GGATGTGCTG GATGTTCCCG AGGGCACCTT    1920

GCCTGACAAA CAGAGCACTG AGCAAGCCAT ACAGTTGTTG GAAAAGATGA AAACGTCAGC    1980

CAGTCCTTTC TTCCTGGCCG TTGGGTATCA TAAGCCACAC ATCCCCTTCA GATACCCCAA    2040

GGTGAAGAGC TGGTTGAGGG CTGATCCAGC ACAGCTGTGA CAGCTGTGTT GTTTGTTGAG    2100

GGAGGGATTT GCACAGGGAA GGTGGCTACA TCCTGCCATC GCCAGGCACC ATGGTTGCCT    2160

GATGGGCACT AGTGTCCTCA GTGGAGTAAA GATGGGATTT AGAGGTAAAA GGCAGTATAG    2220

ACAGTGATAG AGCCACAAGC TTGTGCTTTT GCTAAAAGAG TGACAACTTT GTGGCTTTGT    2280

GTTTTTCCCC AAGGAATTTC AGAAGTTGTA TCCCTTGGAG AACATCACCC TGGCCCCCGA    2340

TCCCGAGGTC CCTGATGGCC TACCCCTGT GGCCTACAAC CCCTGGATGG ACATCAGGCA    2400

ACGGAAGAC GTCCAAGCCT TAAACATCAG TGTGCCGTAT GGTCCAATTC CTGTGGACTT    2460

TCAGGTATCA AGGACATAGT TTGGGGATGT ATTGGACACT GATGACATAG TGTCGTAGGT    2520

GAAACCACTC TTCTCAGTAG ACACAACTCC ACCTATAATG TCTTATTAAG AGCTTTCTTT    2580

GTGTGTAGGG ATTGGGAGAG ATGCACACGG CAAGCATTAT CTCTGTATGC CTTGGCAATT    2640

TAAATTGCAG TCACTCTCAT TTTTATTTTT TTTCAATTTG CAGCGGAAAA TCCGCCAGAG    2700

CTACTTTGCC TCTGTGTCAT ATTTGGATAC ACAGGTCGGC CGCCTCTTGA GTGCTTTGGA    2760

CGATCTTCAG CTGGCCAACA GCACCATCAT TGCATTTACC TCGGATCATG GTAAGCATTT    2820

TGAAATTCCC TGGTGAGTCA AAACATCTGA ACTTTCCTGT GAAACATGCT TTGCAAAATT    2880

GCCATTGACA TAAACATGGG TGTGTTTCTT CTAGGTGATG AGTTTCTACT TCCTCTGGTT    2940

TTTACAACAG GAAATGAAAT GGTATCTAAA ATAAACAAGC TGTGGTATGA TGATTATTCA    3000

TTTTCTGTCA TTCTGTGCTT TTTATGAACT AGGGTGGGCT CTAGGTGAAC ATGGAGAATG    3060

GGCCAAATAC AGCAATTTTG ATGTTGCTAC CCATGTTCCC CTGATATTCT ATGTTCCTGG    3120

AAGGACGGCT TCACTTCCGG AGGCAGGCGA GAAGCTTTTC CCTTACCTCG ACCCTTTTGA    3180

TTCCGCCTCA CAGTTGATGG AGCCAGGTAT AAAATATGCT GAAATGATAT TGCTTGACAG    3240

TAAGATCACC TTTAGTTTAT ATGTGAACCA CTTTATTGAA TCATAGGCTT TGGGGTTACA    3300

CAGACCCCAA AGATAAATGG TGTAAATTAA AAAAGAAAA CATATGGAGC CCAGACAGGG    3360

TCCTTTACTG CTCCTGCCTG GCCATGGCAG GCTTTTATAA TGTAACCCAT TCTGCTCTGT    3420

CGCTTCCTGT TTCAGGCAGG CAATCCATGG ACCTTGTGGA ACTTGTGTCT CTTTTTCCCA    3480

CGCTGGCTGG ACTTGCAGGA CTGCAGGTTC CACCTCGCTG CCCCGTTCCT TCATTTCACG    3540

TTGAGCTGTG CAGAGAAGGC AAGAACCTTC TGAAGCATTT TCGATTCCGT GACTTGGAAG    3600
```

```
AGGATCCGTA CCTCCCTGGT AATCCCCGTG AACTGATTGC CTATAGCCAG TATCCCCGGC    3660

CTTCAGACAT CCCTCAGTGG AATTCTGACA AGCCGAGTTT AAAAGATATA AAGATCATGG    3720

GCTATTCCAT ACGCACCATA GACTATAGGT ATACTGTGTG GGTTGGCTTC AATCCTGATG    3780

AATTTCTAGC TAACTTTTCT GACATCCATG CAGGGGAACT GTATTTTGTG GATTCTGACC    3840

CATTGCAGGA TCACAATATG TATAATGATT CCCAAGGTGG AGATCTTTTC CAGTTGTTGA    3900

TGCCTTGAGT TTTGCCAACC ATGGATGGCA AATGTGATGT GCTCCCTTCC AGCTGGTGAG    3960

AGGAGGAGTT AGAGCTGGTC GTTTTGTGAT TACCCATAAT ATTGGAAGCA GCCTGAGGGC    4020

TAGTTAATCC AAACATGCAT CAACAATTTG GCCTGAGAAT ATGTAACAGC CAAACCTTTT    4080

CGTTTAGTCT TTATTAAAAT TTATAATTGG TAATTGGACC AGTTTTTTTT TTAATTTCCC    4140

TCTTTTTAAA ACAGTTACGG CTTATTTACT GAATAAATAC AAAGCAAACA AACTCAAGTT    4200

ATGTCATACC TTTGGATACG AAGACCATAC ATAATAACCA AACATAACAT TATACACAAA    4260

GAATACTTTC ATTATTTGTG GAATTTAGTG CATTTCAAAA AGTAATCATA TATCAAACTA    4320

GGCACCACAC TAAGTTCCTG ATTATTTTGT TTATAATTTA ATAATATATC TTATGAGCCC    4380

TATATATTCA AAATATTATG TTAACATGTA ATCCATGTTT CTTTTTCC               4428
```

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Pro Arg Glu Leu Ile Ala Tyr Ser Xaa Tyr Pro Arg Xaa Xaa Ile Pro
1               5                  10                  15
```

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Cys Thr Pro Ser Arg
1               5
```

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Gly Lys Trp His Leu Gly
1               5
```

(2) INFORMATION FOR SEQ ID NO:10:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

GGCCTCTAGA CCAGCTACAG TCGGAAACCA TCAGCAAGCA GGTCATTGTT CCAACATGCC    60

GCCACCCCGG ACCGGCCGAG G                                             81

(2) INFORMATION FOR SEQ ID NO:11:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Thr Arg Arg Pro Asn Val Val Leu Leu Leu Thr Asp Asp Gln Asp Glu
1               5                   10                  15

Val Leu Gly Gly Met Thr Pro Leu Lys Lys Thr Lys Ala Leu Ile Gly
            20                  25                  30

Glu Met Gly Met Thr Phe Ser Ser Ala Tyr Val Pro Ser Ala Leu Cys
        35                  40                  45

Cys Pro Ser Arg Ala Ser Ile Leu Thr Gly Lys Tyr Pro His Asn His
    50                  55                  60

His Val Val Asn Asn Thr Leu Glu Gly Asn Cys Ser Ser Lys Ser Trp
65                  70                  75                  80

Gln Lys Ile Gln Glu Pro Asn Thr Phe Pro Ala Ile Leu Arg Ser Met
                85                  90                  95

Gln Gly Tyr Gln Thr Phe Thr Phe Phe Ala Gly Lys Tyr Leu Asn Glu
            100                 105                 110

Tyr Gly Ala Pro Asp Ala Gly Gly Leu Glu His Val Pro Leu Gly Trp
        115                 120                 125

Ser Tyr Trp Tyr Ala Leu Glu Lys Asn Ser Lys Tyr Tyr Asn Tyr Thr
    130                 135                 140

Leu Ser Ile Asn Gly Lys Ala Arg Lys His Gly Glu Asn Tyr Ser Val
145                 150                 155                 160

Asp Tyr Leu Thr Asp Val Leu Ala Asn Val Ser Leu Asp Phe Leu Asp
                165                 170                 175

Tyr Lys Ser Asn Glu Glu Pro Phe Phe Met Met Ile Ala Thr Pro Ala
            180                 185                 190

Pro His Ser Pro Trp Thr Ala Ala Pro Gln Tyr Gln Lys Ala Phe Gln
        195                 200                 205

Asn Val Phe Ala Pro Arg Asn Lys Asn Phe Asn Ile His Gly Thr Asn
    210                 215                 220

Lys His Trp Leu Ile Arg Gln Ala Lys Thr Pro Met Thr Asn Ser Ser
225                 230                 235                 240

Ile Gln Phe Leu Asp Asn Ala Phe Arg Lys Arg Trp Gln Thr Leu Leu
                245                 250                 255

Ser Val Asp Asp Leu Val Glu Lys Leu Val Lys Arg Leu Glu Phe Thr
            260                 265                 270

-continued

```
Gly Glu Leu Asn Asn Thr Tyr Ile Phe Tyr Thr Ser Asp Asn Gly Tyr
            275                 280                 285

His Thr Gly Gln Phe Ser Leu Pro Ile Asp Lys Arg Gln Leu Tyr Glu
        290                 295                 300

Phe Asp Ile Lys Val Pro Leu Leu Val Arg Gly Pro Gly Ile Lys Pro
305                 310                 315                 320

Asn Gln Thr Ser Lys Met Leu Val Ala Asn Ile Asp Leu Gly Pro Ile
                325                 330                 335

Leu Asp Ile Ala Gly Tyr Asp Leu Asn Lys Thr Gln Met Asp Gly Met
            340                 345                 350

Ser Leu Leu Pro Ile Leu Arg Gly Ala Ser Asn Leu Thr Trp Arg Ser
        355                 360                 365

Asp Val Leu Val Glu Tyr Gln Gly Glu Gly Arg Asn Val Thr Asp Pro
    370                 375                 380

Thr Cys Pro Ser Leu Ser Pro Gly Val Ser Gln Cys Phe Pro Asp Cys
385                 390                 395                 400

Val Cys Glu Asp Ala Tyr Asn Asn Thr Tyr Ala Cys Val Arg Thr Met
                405                 410                 415

Ser Ala Leu Trp Asn Leu Gln Tyr Cys Glu Phe Asp Asp Gln Glu Val
            420                 425                 430

Phe Val Glu Val Tyr Asn Leu Thr Ala Asp Pro Asp Gln Ile Thr Asn
        435                 440                 445

Ile Ala Lys Thr Ile Asp Pro Glu Leu Leu Gly Lys Met Asn Tyr Arg
    450                 455                 460

Leu Met Met Leu Gln Ser Cys Ser Gly Pro Thr Cys Arg Thr Pro Gly
465                 470                 475                 480

Val Phe Asp Pro Gly Tyr Arg Phe Asp Pro Arg Leu Met Phe Ser Asn
                485                 490                 495

Arg Gly Ser Val Arg Thr Arg Arg Phe Ser Lys His Leu Leu
            500                 505                 510

(2) INFORMATION FOR SEQ ID NO:12:

(i) SEQUENCE CHARACTERISTICS:
        (A) LENGTH: 507 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Met Gly Ala Pro Arg Ser Leu Leu Leu Ala Leu Ala Ala Gly Leu Ala
1               5                   10                  15

Val Ala Arg Pro Pro Asn Ile Val Leu Ile Phe Ala Asp Asp Leu Gly
            20                  25                  30

Tyr Gly Asp Leu Gly Cys Tyr Gly His Pro Ser Ser Thr Thr Pro Asn
        35                  40                  45

Leu Asp Gln Leu Ala Ala Gly Gly Leu Arg Phe Thr Asp Phe Tyr Val
    50                  55                  60

Pro Val Ser Leu Gln Thr Pro Ser Arg Ala Ala Leu Leu Thr Gln Arg
65                  70                  75                  80

Leu Pro Val Arg Met Gly Met Tyr Pro Gly Val Leu Val Pro Ser Ser
                85                  90                  95

Arg Gly Gly Leu Pro Leu Glu Glu Val Thr Val Ala Glu Val Leu Ala
            100                 105                 110
```

```
Ala Arg Gly Tyr Leu Thr Gly Met Ala Gly Lys Trp His Leu Gly Val
        115                 120                 125

Gly Pro Glu Gly Ala Phe Leu Pro Pro His Gln Gly Phe His Arg Phe
130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Cys Asp Gln Gly Leu
                165                 170                 175

Val Pro Ile Pro Leu Leu Ala Asn Leu Ser Val Glu Ala Gln Pro Pro
                180                 185                 190

Trp Leu Pro Gly Leu Glu Ala Arg Tyr Met Ala Phe Ala His Asp Leu
        195                 200                 205

Met Ala Asp Ala Gln Arg Gln Asp Arg Pro Phe Phe Leu Tyr Tyr Ala
        210                 215                 220

Ser His His Thr His Tyr Pro Gln Phe Ser Gly Gln Ser Phe Ala Glu
225                 230                 235                 240

Arg Ser Gly Arg Gly Pro Phe Gly Asp Ser Leu Met Glu Leu Asp Ala
                245                 250                 255

Ala Val Gly Thr Leu Met Thr Ala Ile Gly Asp Leu Gly Leu Leu Glu
                260                 265                 270

Glu Thr Leu Val Ile Phe Thr Ala Asp Asn Gly Pro Glu Thr Met Arg
        275                 280                 285

Met Ser Arg Gly Gly Cys Ser Gly Leu Leu Arg Cys Gly Lys Gly Thr
        290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
                325                 330                 335

Leu Pro Thr Leu Ala Ala Leu Ala Gly Ala Pro Leu Pro Asn Val Thr
                340                 345                 350

Leu Asp Gly Phe Asp Leu Arg Pro Pro Ala Ala Gly His Arg Gln Glu
        355                 360                 365

Pro Ser Ala Val Ser Leu Leu Leu Pro Val Leu Pro Arg Arg Gly Pro
370                 375                 380

Trp Gly Phe Cys Cys Ala Asp Trp Lys Val Gln Gly Ser Leu Leu His
385                 390                 395                 400

Pro Gly Ser Ala His Ser Asp Thr Thr Ala Asp Pro Ala Cys His Ala
                405                 410                 415

Ser Ser Ser Leu Thr Ala His Glu Pro Pro Leu Leu Tyr Asp Leu Ser
                420                 425                 430

Lys Asp Pro Gly Glu Asn Tyr Asn Leu Leu Gly Gly Val Ala Gly Ala
        435                 440                 445

Thr Pro Glu Val Leu Gln Ala Leu Lys Gln Leu Gln Leu Leu Lys Ala
450                 455                 460

Gln Leu Asp Ala Ala Val Thr Phe Gly Pro Ser Gln Val Ala Arg Gly
465                 470                 475                 480

Glu Asp Pro Ala Leu Gln Ile Cys Cys His Pro Gly Cys Thr Pro Arg
                485                 490                 495

Pro Ala Cys Cys His Cys Pro Asp Pro His Ala
                500                 505
```

(2) INFORMATION FOR SEQ ID NO:13:

(i) SEQUENCE CHARACTERISTICS:

-continued

```
    (A) LENGTH: 533 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:13:
```

Met Gly Pro Arg Gly Ala Ala Ser Leu Pro Arg Gly Pro Gly Pro Arg
1               5                  10                 15

Arg Leu Leu Leu Pro Val Val Leu Pro Leu Leu Leu Leu Leu Leu Leu
           20                  25                  30

Ala Pro Pro Gly Ser Gly Ala Gly Ala Ser Arg Pro Pro His Leu Val
           35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
                85                  90                  95

Gln Leu Leu Thr Gln Arg Tyr Gln Ile Arg Thr Gly Leu Gln His Gln
                100                 105                 110

Ile Ile Trp Pro Cys Gln Pro Ser Cys Val Pro Leu Asp Glu Lys Leu
            115                 120                 125

Leu Pro Gln Leu Leu Lys Glu Ala Gly Tyr Thr Thr His Met Val Gly
130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
                165                 170                 175

Ser His Glu Arg Cys Thr Leu Ile Asp Ala Leu Asn Val Thr Arg Cys
                180                 185                 190

Ala Leu Asp Phe Arg Asp Gly Glu Glu Val Ala Thr Gly Tyr Lys Asn
            195                 200                 205

Met Tyr Ser Thr Asn Ile Phe Thr Lys Arg Ala Ile Ala Leu Ile Thr
210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Glu Tyr Leu Lys Pro Tyr Asp
                245                 250                 255

Phe Ile Gln Asp Lys Asn Arg His His Tyr Ala Gly Met Val Ser Leu
                260                 265                 270

Met Asp Glu Ala Val Gly Asn Val Thr Ala Ala Leu Lys Ser Ser Gly
            275                 280                 285

Leu Trp Asn Asn Ile Val Phe Ile Phe Ser Thr Asp Asn Gly Gly Gln
290                 295                 300

Thr Leu Ala Gly Gly Asn Asn Trp Pro Leu Arg Gly Arg Lys Trp Ser
305                 310                 315                 320

Leu Trp Glu Gly Gly Val Arg Gly Val Gly Phe Val Ala Ser Pro Leu
                325                 330                 335

Leu Lys Gln Lys Gly Val Lys Asn Arg Glu Leu Ile His Ile Ser Asp
                340                 345                 350

Trp Leu Pro Thr Leu Val Lys Leu Ala Arg Gly His Thr Asn Gly Thr
            355                 360                 365

Lys Pro Leu Asp Gly Phe Asp Val Trp Lys Thr Ile Ser Glu Gly Ser

```
                        370                 375                 380
Pro Ser Pro Arg Ile Glu Leu Leu His Asn Ile Asp Pro Asn Phe Val
385                 390                 395                 400

Asp Ser Ser Pro Cys Pro Arg Asn Ser Met Ala Pro Ala Lys Asp Asp
                405                 410                 415

Ser Ser Leu Pro Glu Tyr Ser Ala Phe Asn Thr Ser Val His Ala Ala
                420                 425                 430

Ile Arg His Gly Asn Trp Lys Leu Leu Thr Gly Tyr Pro Gly Cys Gly
            435                 440                 445

Tyr Trp Phe Pro Pro Ser Gln Tyr Asn Val Ser Glu Ile Pro Ser
            450                 455                 460

Ser Asp Pro Pro Thr Lys Thr Leu Trp Leu Phe Asp Ile Asp Arg Asp
465                 470                 475                 480

Pro Glu Glu Arg His Asp Leu Ser Arg Glu Tyr Pro His Ile Val Thr
                485                 490                 495

Lys Leu Leu Ser Arg Leu Gln Phe Tyr His Lys His Ser Val Pro Val
                500                 505                 510

Tyr Phe Pro Ala Gln Asp Pro Arg Cys Asp Pro Lys Ala Thr Gly Val
            515                 520                 525

Trp Gly Pro Trp Met
        530
```

(2) INFORMATION FOR SEQ ID NO:14:

(i) SEQUENCE CHARACTERISTICS:
        (A) LENGTH: 583 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Pro Leu Arg Lys Met Lys Ile Pro Phe Leu Leu Leu Phe Phe Leu
1               5                   10                  15

Trp Glu Ala Glu Ser His Ala Ala Ser Arg Pro Asn Ile Ile Leu Val
                20                  25                  30

Met Ala Asp Asp Leu Gly Ile Gly Asp Pro Gly Cys Tyr Gly Asn Lys
            35                  40                  45

Thr Ile Arg Thr Pro Asn Ile Asp Arg Leu Ala Ser Gly Gly Val Lys
50                  55                  60

Leu Thr Gln His Leu Ala Ala Ser Pro Leu Cys Ile Pro Ser Arg Ala
65                  70                  75                  80

Ala Phe Met Thr Gly Arg Tyr Pro Val Arg Ser Gly Met Ala Ser Trp
                85                  90                  95

Ser Arg Thr Gly Val Phe Leu Phe Thr Ala Ser Ser Gly Gly Leu Pro
                100                 105                 110

Thr Asp Glu Ile Thr Phe Ala Lys Leu Leu Lys Asp Gln Gly Tyr Ser
            115                 120                 125

Thr Ala Leu Ile Gly Lys Trp His Leu Gly Met Ser Cys His Ser Lys
130                 135                 140

Thr Asp Phe Cys His His Pro Leu His His Gly Phe Asn Tyr Phe Tyr
145                 150                 155                 160

Gly Ile Ser Leu Thr Asn Leu Arg Asp Cys Lys Pro Gly Glu Gly Ser
                165                 170                 175

Val Phe Thr Thr Gly Phe Lys Arg Leu Val Phe Leu Pro Leu Gln Ile
```

```
            180                 185                 190
Val Gly Val Thr Leu Leu Thr Leu Ala Ala Leu Asn Cys Leu Gly Leu
                195                 200                 205
Leu His Val Pro Leu Gly Val Phe Phe Ser Leu Leu Phe Leu Ala Ala
    210                 215                 220
Leu Ile Leu Thr Leu Phe Leu Gly Phe Leu His Tyr Phe Arg Pro Leu
225                 230                 235                 240
Asn Cys Phe Met Met Arg Asn Tyr Glu Ile Ile Gln Gln Pro Met Ser
                245                 250                 255
Tyr Asp Asn Leu Thr Gln Arg Leu Thr Val Glu Ala Ala Gln Phe Ile
            260                 265                 270
Gln Arg Asn Thr Glu Thr Pro Phe Leu Leu Val Leu Ser Tyr Leu His
        275                 280                 285
Val His Thr Ala Leu Phe Ser Ser Lys Asp Phe Ala Gly Lys Ser Gln
    290                 295                 300
His Gly Val Tyr Gly Asp Ala Val Glu Met Asp Trp Ser Val Gly
305                 310                 315                 320
Gln Ile Leu Asn Leu Leu Asp Glu Leu Arg Leu Ala Asn Asp Ile Leu
                325                 330                 335
Ile Tyr Phe Thr Ser Asp Gln Gly Ala His Val Glu Glu Val Ser Ser
            340                 345                 350
Lys Gly Glu Ile His Gly Gly Ser Asn Gly Ile Tyr Lys Gly Gly Lys
        355                 360                 365
Ala Asn Asn Trp Glu Gly Gly Ile Arg Val Pro Gly Ile Leu Arg Trp
    370                 375                 380
Pro Arg Val Ile Gln Ala Gly Gln Lys Ile Asp Glu Pro Thr Ser Asn
385                 390                 395                 400
Met Asp Ile Phe Pro Thr Val Ala Lys Leu Ala Gly Ala Pro Leu Pro
                405                 410                 415
Glu Asp Arg Ile Ile Asp Gly Arg Asp Leu Met Pro Leu Leu Glu Gly
            420                 425                 430
Lys Ser Gln Arg Ser Asp His Glu Phe Leu Phe His Tyr Cys Asn Ala
        435                 440                 445
Tyr Leu Asn Ala Val Arg Trp His Pro Gln Asn Ser Thr Ser Ile Trp
    450                 455                 460
Lys Ala Phe Phe Phe Thr Pro Asn Phe Asn Pro Val Gly Ser Asn Gly
465                 470                 475                 480
Cys Phe Ala Thr His Val Cys Phe Cys Phe Gly Ser Tyr Val Thr His
                485                 490                 495
His Asp Pro Pro Leu Leu Phe Asp Ile Ser Lys Asp Pro Arg Glu Arg
            500                 505                 510
Asn Pro Leu Thr Pro Ala Ser Glu Pro Arg Phe Tyr Glu Ile Leu Lys
        515                 520                 525
Val Met Gln Glu Ala Ala Asp Arg His Thr Gln Thr Leu Pro Glu Val
    530                 535                 540
Pro Asp Gln Phe Ser Trp Asn Asn Phe Leu Trp Lys Pro Trp Leu Gln
545                 550                 555                 560
Leu Cys Cys Pro Ser Thr Gly Leu Ser Cys Gln Cys Asp Arg Glu Lys
                565                 570                 575
Gln Asp Lys Arg Leu Ser Arg
            580

(2) INFORMATION FOR SEQ ID NO:15:
```

(i) SEQUENCE CHARACTERISTICS:
  (A) LENGTH: 551 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:15:

```
Met Lys Ser Ala Pro Phe Leu Phe Leu Leu Gly Leu Gly Leu Val
 1               5                  10                  15

Thr Ala Gln Thr Gln Asp Pro Ala Leu Leu Asp Leu Leu Arg Glu Asn
                20                  25                  30

Pro Asp Leu Leu Ser Leu Leu Gln Ser Asn Glu His Arg Ala Pro
                35                  40                  45

Leu Val Lys Pro Asn Val Val Leu Leu Val Ala Asp Asp Met Gly Ser
     50                  55                  60

Gly Asp Leu Thr Ser Tyr Gly His Pro Thr Gln Glu Ala Gly Phe Ile
 65                  70                  75                  80

Asp Lys Met Ala Ala Glu Gly Leu Arg Phe Thr Asn Gly Tyr Val Gly
                85                  90                  95

Asp Ala Val Cys Thr Pro Ser Arg Ser Ala Ile Met Ile Gly Arg Leu
                100                 105                 110

Pro Val Arg Ile Gly Thr Phe Gly Glu Thr Arg Val Phe Leu Pro Trp
                115                 120                 125

Thr Lys Thr Gly Leu Pro Lys Ser Glu Leu Thr Ile Ala Glu Ala Met
                130                 135                 140

Lys Glu Ala Gly Tyr Ala Ile Gly Met Val Gly Lys Trp His Leu Gly
145                 150                 155                 160

Met Asn Glu Asn Ser Ser Ile Asp Gly Ala His Leu Pro Phe Asn His
                165                 170                 175

Gly Phe Asp Phe Val Gly His Asn Leu Pro Phe Thr Asn Ser Trp Ser
                180                 185                 190

Cys Asp Asp Thr Gly Leu His Lys Asp Phe Pro Asp Ser Gln Arg Cys
                195                 200                 205

Tyr Leu Tyr Val Asn Ala Thr Leu Val Ser Gln Pro Tyr Gln His Lys
                210                 215                 220

Gly Leu Thr Gln Leu Phe Thr Asp Asp Ala Leu Gly Phe Ile Glu Asp
225                 230                 235                 240

Asn His Ala Asp Pro Phe Phe Leu Tyr Val Ala Phe Ala His Met His
                245                 250                 255

Thr Ser Leu Phe Ser Ser Asp Asp Phe Ser Cys Thr Ser Arg Arg Gly
                260                 265                 270

Arg Tyr Gly Asp Asn Leu Leu Glu Met His Asp Ala Val Asp Lys Ile
                275                 280                 285

Val Asp Lys Leu Glu Glu Asn Asn Ile Ser Glu Asn Ile Ile Phe
                290                 295                 300

Phe Ile Ser Asp His Gly Pro His Arg Glu Tyr Cys Glu Gly Gly
305                 310                 315                 320

Asp Ala Ser Ile Phe Arg Gly Gly Lys Ser His Ser Trp Glu Gly Gly
                325                 330                 335

His Arg Ile Pro Tyr Ile Val Tyr Trp Pro Gly Thr Ile Ser Pro Gly
                340                 345                 350

Ile Ser Asn Glu Ile Val Thr Ser Met Asp Ile Ile Ala Ile Ala Ala
                355                 360                 365
```

```
Asp Leu Gly Gly Thr Thr Leu Pro Thr Asp Arg Ile Tyr Asp Gly Lys
    370                 375                 380

Ser Ile Lys Asp Val Leu Leu Glu Gly Ser Ala Ser Pro His Ser Ser
385                 390                 395                 400

Phe Phe Tyr Tyr Cys Lys Asp Asn Leu Met Ala Val Arg Val Gly Lys
                405                 410                 415

Tyr Lys Ala His Phe Arg Thr Gln Arg Val Arg Ser Gln Asp Glu Tyr
                420                 425                 430

Gly Leu Glu Cys Ala Gly Gly Phe Pro Leu Glu Asp Tyr Phe Asp Cys
            435                 440                 445

Asn Asp Cys Glu Gly Asp Cys Val Thr Glu His Asp Pro Pro Leu Leu
    450                 455                 460

Phe Asp Leu Met Arg Asp Pro Gly Glu Ala Tyr Pro Leu Glu Ala Cys
465                 470                 475                 480

Gly His Glu Asp Val Phe Leu Thr Val Lys Ser Thr Val Glu Glu His
                485                 490                 495

Lys Ala Ala Leu Val Lys Cys Thr Pro Leu Leu Asp Ser Phe Asp His
                500                 505                 510

Ser Ile Val Pro Cys Cys Asn Pro Ala Asn Cys Cys Ile Cys Asn Tyr
            515                 520                 525

Val His Glu Pro Gly Met Pro Glu Cys Tyr Gln Asp Gln Val Ala Thr
    530                 535                 540

Ala Ala Arg His Tyr Arg Pro
545                 550
```

GLYCOSYLATION VARIANTS OF IDURONATE 2-SULFATASE

CROSS REFERENCE TO RELATED APPLICATION

This application is a continuation application of U.S. Ser. No. 08/345,212 filed on Nov. 28, 1994 now U.S. Pat. No. 5,932,211 issued Aug. 3, 1999 which is a continuation of U.S. Ser. No. 07/991,973 filed Dec. 17, 1992 abandoned which is a continuation-in-part of U.S. Ser. No. 07/790,362 filed on Nov. 12, 1991, abandoned.

FIELD OF THE INVENTION

The present invention relates to glycosylation variants of iduronate-2-sulfatase and to genetic sequences encoding same. The present invention also contemplates the use of these in the treatment and diagnosis of subjects suspected of, or suffering from, iduronate-2-sulfatase deficiency.

BACKGROUND TO INVENTION

Iduronate-2-sulfatase (hereinafter abbreviated to "IDS"; EC 3.1.6.13) acts as an exosulfatase in lysosomes to hydrolyze the C2-sulfate ester bond from non-reducing-terminal iduronic acid residues in the glycosaminoglycans heparan sulfate and dermatan sulfate (1). IDS is one of a family of at least nine sulfatases that hydrolyze sulfate esters in human cells. They are all lysosomal enzymes that act on sulfated monosaccharide residues in a variety of complex substrates with the exception of microsomal steroid sulfatase (or arylsulfatase C), which acts on sulfated 3β-hydroxysteriods (1,2). Each sulfatase displays absolute substrate specificity, making the sulfatase family an attractive model to investigate the molecular requirements for substrate binding and the catalysis of sulfate ester hydrolysis.

A deficiency in the activity of IDS in humans leads to the lysosomal accumulation of heparan sulfate and dermatan sulfate fragments and their excretion in urine (1). This storage results in the clinical disorder Hunter syndrome (mucopolysaccharidosis type II, MPS-II) in which patients may present with variable phenotypes from severe mental retardation, skeletal deformities, and stiff joints to a relatively mild course (1). It has been postulated that this clinical heterogeneity reflects different mutations at the IDS locus affecting enzyme expression, stability, or function. MPS-II is one of the most common mucopolysaccharidoses and is the only one that is X chromosome-linked (1).

In accordance with the present invention, there is provided the nucleotide sequence for a full length cDNA clone for IDS from human endothelial cells. The present invention also provides the genomic clone for IDS. More particularly, following expression of the IDS nucleotide sequence in particular cell lines, a glycosylation variant of IDS has been isolated which possesses inter alia improved half-life and/or improved uptake properties when compared to the naturally glycosylated molecule.

SUMMARY OF THE INVENTION

One aspect of the present invention provides a recombinant human iduronate-2-sulfatase (IDS) or a fragment thereof retaining enzymatic activity wherein said recombinant IDS or fragment thereof is more highly glycosylated than the naturally occurring enzyme or equivalent fragment on the naturally occurring enzyme.

Another aspect of the present invention contemplates a method for treating a patient suffering from iduronate-2-sulfatase (IDS) deficiency said method comprising administering to said patient an effective amount of a recombinant human IDS or a fragment thereof retaining enzymatic activity wherein said recombinant IDS or fragment thereof is more highly glycosylated than the naturally occurring enzyme or equivalent fragment on the naturally occurring enzyme.

Yet another aspect of the present invention is directed to a pharmaceutical composition useful in the treatment of patients suffering from iduronate-2-sulfatase (IDS) deficiency said composition comprising the more highly glycosylated IDS or enzymatically active fragment thereof referred to above and one or more pharmaceutically acceptable carriers and/or diluents.

Still yet another aspect of the present invention provides an isolated genomic DNA fragment carrying in whole or in part the IDS gene or a mutant or derivative thereof. The isolation of the genomic clone will enable gene therapy and genetic analysis of IDS deficiency diseases.

BRIEF DESCRIPTION OF THE FIGURES

FIG. 1 is a representation of compiled nucleotide sequence SEQ ID NO: 1 of the IDS cDNA clones and the deduced amino acid sequence of the encoded protein SEQ ID NO: 2. Amino acid sequence is shown in the one-letter code above the nucleotide sequence. Nucleotide and amino acid numbers are depicted on the right margin. Possible sites for peptidase cleavage of the signal peptide are indicated with arrows. Underlined amino acids are colinear with amino-terminal sequences (14 kDa, Pro-Art-Glu-Leu-Ile-Ala-Tyr-Ser-Xaa-Tyr-Pro-Arg-Xaa-Xaa-Ile-Pro, determined SEQ ID NO: 3 by direct sequence analysis). Potential N-glycosylation sites are starred. A potential polyadenylation signal is doubly underlined.

FIG. 3 is a representation showing alignment of amino acid sequences of human IDS, human glucosamine 6-sulfatase (19), human galactose 3-sulfatase or arylsulfatase A (14), human N-acetylgalactosamine 4-sulfatase or arylsulfatase B (15), human steroid sulfatase or arylsulfatase C (20, 21), and sea urchin arylsulfatase (22) shown in lines 2, 6, A, B C and U, respectively. Amino acids identical in all sulfatases are boxed. Amino acids identical in the arylsulfatase activities (lines A, B, C, and U) are starred on the bottom line. The ringed residues in lines 2, 6 and B indicate the first amino-terminal amino acid in polypeptides produced by internal proteolysis. Underlined sequences are unique to each particular sulfatase sequence and underlined and starred sequences are blocks of conserved residues.

FIG. 7 is a representation of the genomic nucleotide sequence for the IDS gene.

DETAILED DESCRIPTION OF THE INVENTION

Figure 2A:
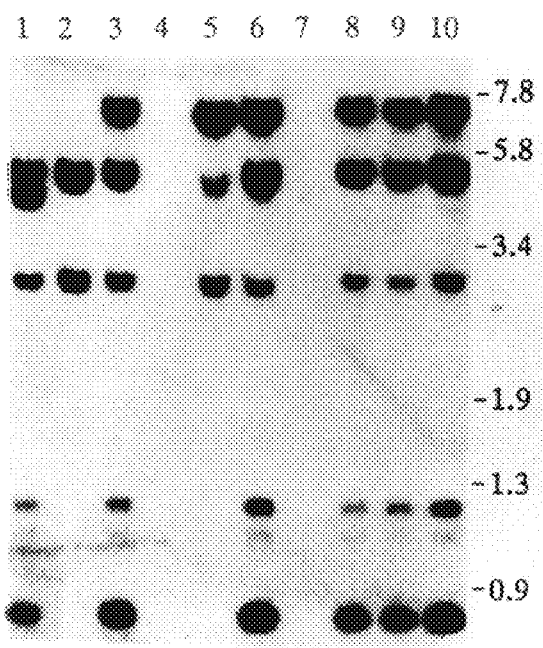
FIG. 2 is a photographic representation showing: (A) Southern blot analysis of MPS-II DNA for deletions and rearrangement of the IDS gene. λc2S15 was used to probe a Southern blot of Pst I-digested DNA samples from a normal male and female (lanes 9 and 10, respectively) and from severely affected MPS-II patients (lanes 1–8). The sizes (kb) of DNA molecular mass standards are shown in the right margin. (B) Northern blot of RNA from human placenta. The size (kb) of each RNA species is shown in the right margin.

The present invention provides an isolated nucleic acid molecule comprising a sequence of nucleotides which encodes or is complementary to a sequence which encodes human IDS or an enzymatically active fragment thereof. More particularly, the present invention is directed to the expression of such a nucleic acid molecule in a host cell which results in the recombinant IDS (rIDS) being more highly glycosylated relative to the extent of glycosylation of the naturally occurring molecule.

When comparing the extent of glycosylation, the reference molecule is either naturally occurring IDS purified, for example, from human liver or may be a recombinant molecule produced in a cell line with an extent of glycosylation similar to the naturally occurring molecule. The critical comparison is not the glycosylation pattern per se but the extent to which the molecule is glycosylated.

Preferably, the more highly glycosylated IDS of the present invention has a molecular weight at least 5 kDa greater than the naturally occurring molecule or its recombinant equivalent, more preferably at least 10 kDa greater, even more preferably at least 15 kDa greater and still even more preferably at least 20–30 kDa greater. Accordingly, the more highly glycosylated IDS has a molecular weight of approximately 65–95 kD or more preferably from about 70 to about 90 kDa depending on the host cell employed. In a most preferred embodiment, the molecular weight is about 90 kDa when produced in CHO-K1 cells or about 70 kDa when produced in CHO-Lec1 cells.

Conveniently, the cDNA encoding IDS or its fragment is modified by replacing the 5' non-coding sequence with a portion of rat pre-pro-insulin leader sequence and inserted into an appropriate expression vector. The modified cDNA is then subject to expression in cell lines capable of more highly glycosylating the resulting recombinant molecule. Although the preferred cell lines described herein are CHO-K1 cells and CHO-Lec1 cells, it would be routine for one skilled in the art to select other cell lines and screen the resulting recombinant IDS to ascertain the extent of glycosylation. All cell lines resulting in a more highly glycosylated IDS are encompassed by the present invention.

The "nucleic acid molecule" of the present invention may be RNA or DNA (eg. cDNA), single or double stranded and linear or covalently closed. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions and/or additions including fragments thereof. All such variations in the nucleic acid molecule retain the ability to encode a more highly glycosylated IDS when expressed in the appropriate host or an enzymatically active fragment of IDS. The enzymatic activity of the resultant molecule is readily ascertained by, for example, using the radiolabelled disaccharide substrate IdoA2S-anM6S of Bielicki et al (3).

The nucleic acid molecule of the present invention may constitute solely the nucleotide sequence encoding human IDS or like molecule or may be part of a larger nucleic acid molecule and extends to the genomic clone of IDS. The non-IDS encoding sequences in a larger nucleic acid molecule may include vector, promoter, terminator, enhancer, replication or signal sequences or non-coding regions of the genomic clone.

In its most preferred embodiment, the cDNA encoding IDS SEQ ID NO: 1 is as set forth in FIG. 1 or having at least 60%, preferably at least 70% and even more preferably at least 80–90% similarity thereto. The genomic sequence encoding IDS is SEQ ID NO: 6, preferably as set forth in FIG. 7 or having similarity thereto as defined above for the cDNA clone.

The present invention is particularly directed to recombinant IDS in more highly glycosylated form as hereinbefore described. The recombinant IDS may comprise an amino acid sequence corresponding to the naturally occurring amino acid sequence or may contain single or multiple amino acid substitutions, deletions and/or additions. The present invention also extends to fragments of the IDS molecule but which retain IDS activity. Such fragments are referred to herein as being "enzymatically active". Accordingly, this aspect of the present invention contemplated a highly glycosylated IDS molecular or enzymatically active fragments or derivatives thereof. The IDS molecule of the present invention, therefore, comprises parts, derivatives and/or portions of the IDS enzyme having enzymatic activity and being more highly glycosylated relative to the naturally occurring enzyme or equivalent fragment or derivative.

Advantageously, the recombinant highly glycosylated IDS is a biologically pure preparation meaning that it has undergone some purification away for other proteins and/or non-proteinacous material. The purity of the preparation may be represented as at least 40% of the enzyme, preferably at least 60%, more preferably at least 75%, even more preferably at least 85% and still more preferably at least 95% relative to non-IDS material as determined by weight, activity, amino acid homology or similarity, antibody reactivity or other convenient means.

Amino acid insertional derivatives of IDS of the present invention include amino and/or carboxy terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Where the enzyme is derivative by amino acid substitution, the amino acids are generally replaced by other amino acids having like properties such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield synthesis) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently elsewhere described such as Sambrook et al, 1989 *Molecular Cloning: A Laboratory Manual* Cold Spring Harbor Laboratories, Cold Spring Harbor, N.Y.

The derivatives of the IDS of the present invention include single or multiple substitutions, deletions and/or additions of any component(s) naturally or artificially associated with the IDS enzyme such as carbohydrate, lipid and/or other proteinaceous moieties. All such molecules are encompassed by the expressions "mutants", "derivatives", "fragments", "portions" and "like" molecules. These molecules are enzymatically active and retain their more highly glycosylated form relative to the naturally occurring enzyme or equivalent derivative when produced in suitable host cells.

The present invention also extends to recombinant IDS molecules when fused to other proteinaceous molecules. The latter may include another enzyme, reporter molecule, purification site or an amino acid sequence which facilitates transport of the molecule out of a cell.

In a most preferred embodiment, the present invention has an amino acid or corresponding IDS cDNA nucleotide sequence substantially as set forth in FIG. 1 or having at least 40% similarity, preferably at least 60% similarity thereto or more preferably at least 80% or 85–90% similarity thereof.

The present invention further contemplates antibodies to the more highly glycosylated IDS. The antibodies may be polyclonal or monoclonal, naturally occurring or synthetic (including recombinant, fragment (eg Fab Fragment) or fusion forms). Such antibodies will be useful in developing immunoassays for IDS and in distinguishing between molecules having an altered extent of glycosylation. Preferably, therefore, the antibody is capable of binding the more highly glycosylated form of IDS but not the naturally glycosylated form of the molecule.

It is within the scope of this invention to include any second antibodies (monoclonal, polyclonal or fragments of antibodies) directed to the first mentioned antibodies discussed above. Both the first and second antibodies may be used in detection assays. Furthermore, the first antibody may be used with a commercially available anti-immunoglobulin antibody. An antibody as contemplated herein includes any antibody specific to the more highly glycosylated form of IDS but not to the normally glycosylated enzyme.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of IDS, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976). Antibodies capable of also binding to the non-highly glycosylated form of IDS can be readily removed, for example, by immuno-adsorbant techniques.

The assay for the highly glycosylated IDS may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the samples containing an IDS to be tested is brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is generally a biological sample comprising biological fluid but also extends to fermentation fluid and supernatant fluid such as from a cell culture.

In the typical forward sandwich assay, a first antibody having specificity for the highly glycosylated IDS, or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes) and under suitable conditions (e.g. 25° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alterative method involved immobilizing the target IDS molecules in the biological sample and then exposing the immobilized target to specific antibody which may or may be not labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to one skilled in the art. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention further contemplates a method of treating a patient suffering from IDS deficiency said method comprising administering to said patient an effective amount of a recombinant human IDS or a fragment thereof retaining enzyme activity where said recombinant IDS or fragment thereof is more highly glycosylated than the naturally occurring enzyme or equivalent fragment of the naturally occurring enzyme.

The highly glycosylated rIDS has enhanced uptake properties and/or a longer in vivo half-life and, hence, is more effacacious than the naturally glycosylated molecule.

Such a highly glycosylated IDS is as herein described. Generally, this aspect of the present invention can be accomplished using a pharmaceutical composition.

Accordingly, another aspect of the present invention contemplates a pharmaceutical composition useful in treating patients suffering from a deficiency in IDS such as in Hunter Syndrome, said composition comprising a recombinant human IDS or a fragment thereof retaining enzyme activity wherein said recombinant IDS or fragment thereof is more highly glycosylated than the naturally occurring enzyme or equivalent fragment of the naturally occurring enzyme, said composition further comprising one or more pharmaceutically acceptable carriers and/or diluents.

The formulation of pharmaceutical composition is generally known in the art and reference can conveniently be made to Remington's Pharmaceutical Sciences, 17th ed., Mack Publishing Co., Easton, Pa., USA.

The active ingredients of a pharmaceutical composition comprising the highly glycosylated IDS or fragments thereof are contemplated to exhibit excellent therapeutic activity, for example, in treating Hunter Syndrome when administered in amount which depends on the particular case. For example, from about 0.5 ug to about 20 mg per patient or per kilogram of body weight of the patient per day, week, or month may be administered. Dosage regima may be adjusted to provide the optimum therapeutic response. For example, several divided doses may be administered daily or the dose may be proportionally reduced as indicated by the exigencies of the therapeutic situation. Depending on the patient or other conditions more preferred dosages comprise 10 μg to 10 mg, 20 μg to 5 mg or 100 μg to 1 mg per patient or per kilogram of body weight of the patient per administration. The composition may be administered an any convenient manner such as by the oral, intravenous (where water soluble), intramuscular, subcutaneous, intranasal, intradermal or suppository routes or implanting (eg using slow release molecules). Depending on the route of administration, the active ingredient which comprises a highly glycosylated IDS or fragment thereof may be required to be coated in a material to protect said ingredients from the action of enzymes, acids and other natural conditions which may inactivate said ingredients. For example, due to the low lipophilicity of IDS, these may potentially be destroyed in the gastrointestinal tract by enzymes capable of cleaving peptide bonds and in the stomach by acid hydrolysis. In order to administer the IDS molecules by other than parenteral administration, they may be coated by, or administered with, a material to prevent its inactivation. For example, the IDS molecules may be administered in an adjuvant, co-administered with enzyme inhibitors or in liposomes. Adjuvant is used in its broadest sense and includes any immune stimulating compound such an interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water emulsions as well as conventional liposomes.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the highly glycosylated recombinant IDS molecules are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, by varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains an effective amount of recombinant IDS as hereinbefore described.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated.

Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg includes 1.0 $\mu$g to 200 mg, 10 $\mu$g to 20 mg and 100 $\mu$g to 10 mg. In the case of compositions containing supplementary active ingredients, the dosages are determined by reference to the usual dose and manner of administration of the said ingredients.

EXAMPLE 1

CLONING OF IDS GENE

1. MATERIALS AND METHODS

Materials.

Form A of IDS was purified from human liver as described (3). Restriction endonucleases, polynucleotide kinase, T4 DNA ligase, the Klenow fragment of DNA polymerase I, and M13 sequencing kits were from Boehringer Mannheim. GeneScreen Plus nylon filters were from DuPont/NEN. [$\gamma$-$^{32}$P]ATP (500 Ci/mmol; 1 Ci=37 GBq), [$\alpha$-$^{32}$P]dCTP (3000 Ci/mmol), and Multiprime DNA labeling kit were from Amersham. Oligo(dt)-cellulose and Sephadex G-50 were from Pharmacia P-L Biochemicals. The X chromosome genomic library LA0XNL01 was from the American Tissue Culture Collection, and the $\lambda$gt10 random-primed human colon cDNA library (1.5×10$^6$ independent clones) and the $\lambda$gt11 human endothelial cDNA library (2.1×10$^6$ independent clones) were from Clontech.

Polypeptide Isolation and Sequencing.

Approximately 20 $\mu$g of form A liver ADS was subjected to a SDS/polyacrylamide gel electrophoresis and transferred to an Immobilon P membrane (Millipore) (4) with modifications of overnight pre-electrophoresis of the SDS/polyacrylamide gel and the addition of 200 $\mu$l of 100 mM sodium thioglycollate to the cathode buffer chamber before electrophoresis. The 42-kDa and the 14-kDa polypeptides were excised and directly amino-terminal sequenced by Bresatec (Adelaide, Australia).

Library Screening.

A 49-mer oligonucleotide sequence SEQ ID NO: 4 (3'-ACTAGTAGCACCTGCTGGACGCCGG-GAGGGACCCGCTGATGCTGCT GCA-5') was designed from the amino-terminal amino acid sequence (SEQ ID NO: 5) (using residues 8–24 of TSALNVLLIIVDDLRPSLGDYDDVL) of the 42-kDa IDS polypeptide. T4 polynucleotide kinase and [$\gamma$-$^{32}$P]ATP were used to end-label the 49-mer to a specific activity greater than 10$^7$ cpm/$\mu$g for screening of the X chromosome library. The bacterial host used was NM538 and 2×10$^5$ recombinants were screened at a density of 30,000 plaque-forming units per 15 cm plate. Positive clones were plaque-purified, DNA was isolated from lysates, and the inserts were separated on 1% w/v agarose and then analysis by Souther blotting using the labeled 49-mer as a probe. A 49-mer positive 1.6-kilobase (kb) HindIII genomic DNA fragment was labeled with [$\alpha$-$^{32}$P]dCTP using a Multiprime DNA labelling kit and used to screen the human colon cDNA library. Approximately 5×10$^5$ recombinants were screened at a density of 55,000 plaque-forming units per 15 cm plate using the bacterial host C600. A 300-base-pair (bp) HindIII-EcoRI fragment from the 3' end of a 1.5-kb colon cDNA clone ($\lambda$c2S15) was labelled and used to screen the human endothelial cDNA library. The bacterial host used was NM538 and 5×10$^5$ recombinants were screened at a density of 40,000 plaque-forming units per 15 cm plate.

Nucleotide Sequencing.

Sonicated DNA fragments generated from the 1.5-kb cDNA insert were subcloned into M13mp19 for nucleotide sequence analysis by the dideoxynucleotide chain-termination method by using the Klenow fragment of DNA polymerase I at 45° C.(5). Some internal regions of the 1.5-kb cDNA were sequenced using primers labeled at their 5' ends with [$\lambda$-$^{32}$P]ATP with single-stranded DNA templates generated by asymmetric polymerase chain reactions. The remaining coding sequence and the 5' and 3' untranslated regions present on the 2.3 kb endothelial cDNA were sequenced using specific primers on M13 subclones.

Southern Blot Analysis of MPS-II Patients.

DNA from MPS-II patients and normal control cultured fibroblasts was prepared and digested with PstI (6) and separated by agarose gel electrophoreses and transferred to GeneScreen Plus nylon membrane. The cDNA fragment $\lambda$c2S15 was radiolabeled using the Multiprime DNA labeling kit and purified by gel filtration on a 1-ml Sephadex G-50 column. The nylon filter was prehybridized, hybridized, and washed according to the manufacturer's instructions.

RNA Isolation and Northern Blot Analysis.

Total RNA was isolated from placental tissue by using a single-step guanidinium thiocyanate method (7). Poly(A)$^+$ RNA was obtained by oligo(dT)-cellulose chromatography and characterized by Northern Blot analysis carried out after electrophoresis in a 0.8% w/v agarose/2.2 M formaldehyde gel and transfer to GeneScreen Plus nylon membrane. Prehybridization, hybridization, and washing were performed according to the manufacturer's instructions. Radiolabeled $\lambda$c2S15, prepared and purified as described above, was used in all hybridization experiments.

Sequence Analysis.

The nucleotide sequence was screened against the GenBank nucleotide sequence data base (Release 62.0, December 1989) and the encoded protein sequence was screened against the National Biomedical Research Foundation protein data base (Release 23.0, December 1989). General sequence analysis and the multiple protein sequence alignment were performed using programs from Reisner and Bucholtz (8) and Lipman et al., (9), respectively.

2. RESULTS

IDS from human liver can be purified to two major forms (A and B) which have different pI values and contain both 42 kDa and 14 kDa polypeptides (3). The 42 kDa and 14 kDa polypeptides in form A were subjected to direct amino-terminal amino acid sequencing and a region of low codon redundancy in the 42 kDa amino-terminal sequence was used to design a single 49-mer oligonucleotide sequence incorporating choices based on human codon usage (10). The 49-mer detected 14 clones when used to screen an X chromosome enriched genomic library. Two overlapping clones were analysed in more detail and found to contain the same 1.6 kb 49-mer positive HindIII fragment. This fragment was shown to give a positive signal when used to probe DNA from a human-mouse cell hybrid that contained the tip of the long arm of the X chromosome (Xq26-ter) consistent with the localisation of the IDS gene to this small portion of the human X chromosome (1).

The 1.6 kd HindIII genomic DNA fragment was then used to screen a human colon cDNA library. Eighteen clones were detected and their inserts were sized. The clone with the longest insert (λ2S15) was fully sequenced and found to contain an initiating methionine and a continuous open reading frame that included a sequence that was colinear with the 42 kDa and the 14 kDa amino-terminal amino acid sequences. However, the reading frame did not extend to include a stop codon of any 3' untranslated region. A 300 bp HindIII-EcoRI restriction fragment from the 3' end of the λc2S15 was then used to screen a cDNA library constructed from human endothelial cells. Twenty seven clones were isolated; 5 of which were also positive to the amino-terminal-specific 49-mer. Of the five, the clone that contained the longest insert (2.3 kb; λc2S23) was sequenced in combination with λc2S15.

FIG. 1 (SEQ ID NO: 1) shows the nucleotide sequence of the 2297 bp insert from λ2S23, which encodes the entire amino acid sequence of IDS. Except for a few differences, the deduced amino acid sequence was colinear with the determined amino-terminal amino acid sequence of the 42 kDa and 14 kDa polypeptides. The amino acid discrepancies (residues 35, 53, 55 and 57) between the direct and predicted amino acid sequence data are believed to reflect amino acid sequencing errors resulting from the low signal obtained toward the end of the amino acid sequencing run. The detection of gene deletions and rearrangements in DNA from a group of severely affected MPS-II patients when hybridised with λc2S15 established that these cDNA clones encoded IDS (FIG. 2A). Of the 23 MPS-II patients analysed, 7 had structural alterations including deletions of the entire λc2S15 coding region. These 7 patients also revealed similar Southern patterns indicative of structural alternations of the ID gene when their DNA was digested with HindIII, StuI and TaqI and probed with λc2S15. Sixteen patients had identical patterns to normal controls, suggesting the presence of small deletions or point mutations responsible for the MPS-II biochemical and clinical phenotype. The two patients, in which the entire IDS gene had been removed (FIG. 2A) had the most severe clinical phenotype of the large group of MPS-II patient studied, raising the possibility that these patients may also have deletions of contiguous genes to IDS.

The sequence of λc2S23 shown in FIG. 1 (SEQ ID NO: 2) contains an open reading frame from the initiation codon at position 125 to the termination codon (TGA) at position 175. This 1650 bp sequence encodes a polypeptide of 550 amino acids as shown.

The sequence flanking the ATG codon at bp 125 SEQ ID NO: 1 is in agreement with the consensus sequence for initiator codons (11). The first 25 amino acids at the amino terminus of the deduced protein have features characteristic of a signal sequence (12). Two putative sites for cleavage between the signal sequence and mature protein are indicated by arrows (FIG. 1). It would appear that eight amino acids are removed from the IDS precursor immediately after the most favored signal peptidase cleavage site (12) between residues 25 and 26. The 14 kDa polypeptide amino-terminal amino acid sequence was identified at amino acid residue 456, giving a total of 95 amino acids to the carboxyl terminus. The full sequence contains eight possible N-glycosylation sites (Asn-Xaa-Ser/Thr, FIG. 1). The molecular weight of the deduced polypeptide for the 14 kDa component was calculated as 11,093. The 14 kDa polypeptide does not contain cysteine residues, which is compatible with the finding that the 42 kDa and the 14 kDa polypeptide are not linked by disulfide bonds (3). The number of potential N-glycosylation sites used in the 42 kDa polypeptide is not known. The first N-glycosylation site (residue 31) is not contained within IDS form A since this asparagine residue is removed during amino-terminal processing. The molecule weight of the deduced peptide for the 42 kDa component was calculated as 47,404, suggesting that the value determined by SDS/polyacrylamide gel electrophoresis (3) may be in error or that additional amino acids are lost during internal proteolytic cleavage of the IDS precursor. These results suggest that post-translational proteolytic processing of IDS is restricted to cleavage of a signal peptide, removal of the amino-terminal 8 amino acids, and internal cleavage to produce the observed 42 and 14 kDa polypeptides in human liver, kidney, lung and placenta (3). This is a commonly observed polypeptide maturation process for lyosomal enzymes that are generally synthesized as larger precursors and then coverted to their mature forms by a limited number of proteolytic steps shortly before or after their transfer into lysosomes (13).

Figure 2B:
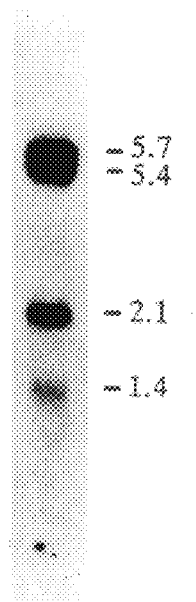

Northern blot analysis of placental poly(A)$^+$ RA with λc2S15 revealed three major RNA species (5.7, 5.4 and 2.1 kb) and one minor species (1.4 kb) (FIG. 2B). It is likely that IDS, like other lysosomal enzymes [e.g., arylsulfatase A, B, and C (14–16)], has mRNA species that differ in length at their 3') ends due to differential polyadenylation. Arylsulfatase C has three major RNA transcripts that result from the use of different polyadenylation sites (2.7, 5.2 and 7.0 kb) the longest of which has a 3' untranslated region of >4 kb (16). Differential polyadenylation can account for the three major species but it cannot explain the 1.4 kb minor species, which is too small to encode the full IDS protein. It is possible that the 1.4 kb species represents a degradation produce or a cross-reacting species, although it is also possible that is results from a process of differential splicing to produce another protein product, as has been observed for the human lysosomal enzymes, for example, β-glucuronidase (17) and β-galactosidase (18). The 520 bp of 3' untranslated region in λc2S23 contains a potential polyadenylation signal (AATAAA) at position 2041 that may direct the position of polyadenylation for the observed 2.1 kb mRNA species. If this is the case, the 124 bp of 5' untranslated region in λc2S23 is sufficient to account for most, if not all, of the 5' untranslated region expected for the 2.1 kb mRNA species [allowing for 50–100 residues of poly(A) tail].

FIG. 3 shows an alignment of IDS amino acid sequence with sequence of other human-derived sulfatases and a sea urchin arylsulfatase. This analysis reveals many areas of identical and conserved amino acid matches within the arylsulfatase group (galactose 3-sulfatase, N-acetylgalactosamine 4-sulfatase and steroid sulfatase) and the two nonarylsulfatase sequences (unpublished data), IDS and glucosamine 6-sulfatase. Sea urchin arylsulfatase is also aligned and has sequence homology with the other five human sulfatases. A multiple sequence alignment of the amino acid sequence of these six sulfatases has the highest level of homology in the amino-terminal third of each sulfatase (FIG. 3). The human arylsulfatase group has conserve blocks of up to six identical amino acid residues, for example, Cys-Thr-Pro-Ser-Arg and Gly-Lys-Trp-His-Leu-Gly (FIG. 3). On the other hand, only part of these sequences are conserved in the two nonarylsulfatases, IDS and glucosamine 6-sulfatase. These sequences may represent regions of the arylsulfatases that enable the relatively non-specific hydrolysis of arylsulfates. All five human sulfatases have significant sequence homology with the amino acid sequence of sea urchin arylsulfatase (FIG. 3). By taking account of conservative amino acid substitutions (23), there are even larger areas of homology within these six sulfatases. This high level of sequence conservation further supports the suggestion that these five human sulfatases are evolutionarily related to a common ancestral gene (14, 15, 19).

There are several regions in FIG. 3 where peptide inserts appear to be unique to a particular sulfatase. For instance, the microsomal membrane-bound steroid sulfatase contains two membrane-spanning regions (FIG. 3) (21). IDS also contains an amino acid sequence insert in the same region as the second membrane-spanning region of steroid sulfatase (FIG. 3). A second peptide insert in IDS is present just before the amino terminal sequence of the 14 kDa polypeptide. The role that these two peptide inserts may have in IDS function is unknown. Interestingly, the sites (ringed in FIG. 3) for internal proteolysis of both glucosamine 6-sulfatase (19) and N-acetylgalactosamine 4-sulfatase also occur near the sequence inserts.

The genomic sequence for IDS was isolated and is set forth in FIG. 7 (and SEQ ID NO: 1).

EXAMPLE 2

PRODUCTION OF HIGHLY GLYCOSYLATED FORMS OF IDS

1. MATERIALS AND METHODS

All enzymes for DNA manipulations, DNAase, dithiothreitol, kanamycin and streptomycin were purchased from Boehringer Mannheim (Dulwich, SA, Australia). DNA oligonucleotides were synthesized using an Applied biosystems 391 DNA Synthesiser. $Na_2{}^{35}SO_4$ (516 mCi/mmol) was purchased from New England Nuclear (Dupont, North Ryde, NSW, Australia). PBE94 chromatofocusing medium, polybuffer 74 and high and low molecular-mass standard kits for SDS-PAGE and gel chromatography were obtained from Pharmacia (North Ryde, NSW, Australia). TSK G3000SW Ultrapac was purchased from LKB (Bromma, Sweden). Blue A matrix agarose gel and ultrafiltration stirred cell model 8200 and Diaflo ultrafiltration membrane YM10 was obtained from Amicon (Danvers, Mass., USA). Dialysis membrane with a 10–12 kDa cut off was obtained from Union Carbide Corp. (Chicago, Ill, USA). Endoglycosidase F was purchased from Nenzymes (DuPont Co., Wilmington, Del., USA). Dulbecco's modified phosphate-buffered saline (PBS) was purchased from Commonwealth Serum Laboratories (Melbourne, Vic., Australia). Nonidet P40, mannose-6-phosphate and BSA were purchased from Sigma (St. Louis, Mo., USA). Basal medium Eagle's (BME), penicillin and glutamine were obtained from Flow Laboratories (Sydney, NSW, Australia) and fetal calf serum (FCS), Ham's F12 nutrient mixture, CHO-SFM medium and G418 (Geneticin) were from Gibco (Glen Waverley, Vic., Australia).

DNA Manipulation and Recombinant Plasmids

All DNA preparation, modification and cloning procedures were done using standard techniques (26). The IDS cDNA clone pB12Sc17 contains bp 107 (NotI restriction enzyme site) to bp 1870 (BstXI restriction enzyme site) of the IDS cDNA of Example 1 (SEQ ID NO: 1), cloned between the NotI and EcoRV restriction enzymes sites of pBlueScript (Stratagene, La Jolla, Calif., USA). The expression vector pRSVN.08 was derived from pRSVN.07 (27) by the introduction of an EcoRV site into the polylinker such that the order of restriction sites is 5' HindIII, XbaI, BamHI, EcoRV, EcoRI, NotI 3'.

Culture and Electroporation of CHO-K1 cells

CHO-K1 cells were cultured and electroporated as previously described (17) unless otherwise stated. Lec 1 cells are available from the New Jersey Cell Line Collection, New Jersey. USA. Under ATCC CRL 1735 and are described in Stanley et al *Somat Cell Genet*. vol 3(1977) pp 391–405.

Culture of fibroblasts

Human diploid fibroblasts were established from skin biopsies submitted to this hospital for diagnosis (28). Cell lines were maintained according to established procedures in BME, 10% v/v FCS and antibiotics unless otherwise stated. The two MPS II skin fibroblast cell lines used in this study (SF-635 and SF-1779) both have low residual IDS activity.

Determination of IDS expression

Media samples, or cell lysates prepared by six cycles of freeze/thaw in 0.5 M-NaCl/20 mM-Tris/HCl, pH 7.0, were clarified by microcentrifugation (12,000×g, 4° C., 5 min) and were either assayed directly or after dilution in assay buffer. Where possible cell lysates were dialysed in 5 mM-sodium acetate, pH 4.0, before assaying as this results in higher measured enzyme activity. IDS was assayed using the radiolabelled disaccharide substrate IdoA2S-anM6S (3). Protein estimations were according to the method of Lowry et al (29).

β-Hexosamidase

The fluorogenic substrate 4-methylumbelliferyl-2-acetamido-2-deoxy-β-D-glucopyranoside was used to measure β-hexosaminidase activity (31).

Correction of MPS II fibroblasts

For these experiments IDS was obtained from CHOEFI2S-9 cells cultured in CHO-SFM medium supplemented with 10 mM-$NH_4Cl$ and antibiotics. The medium was concentrated 10-fold by ultrafiltration and was shown to contain rIDS with activity of $2.75×10^6$ pmol/min per ml (133 µg of I2S/ml). Fibroblasts from a normal individual (SF-3409) and from two MPS II patients (SF-635 and SF-1779) were grown to confluency in 25 cm² flasks and radiolabelled with $Na_2{}^{35}SO_4$ as previously described (27). The labelled cells were then exposed to $5×10^4$ pmol/min per ml of rIDS for 72 hours. After harvesting the cells by trypsin treatment and washing by centrifugation/resuspension in PBS, the cell pellet was resuspended in 100 µl of 20 mM-Tris/HCl, pH 7.0/0.5 M-NaCl, and the cell lysates prepared as described above. The cell extracts were analysed for IDS activity, total protein, β-hexosaminidase activity and radioactivity.

Endocytosis of rIDS

Cells from SF-1779 were plated in 20 wells (3.83 cm²) and allowed to reach confluency. Wells 1 to 4 were untreated controls. To each of wells 5 to 12 and 13 to 20 was added 1.0 ml of medium containing rIDS at $5 \times 10^4$ pmol/min per ml and $5 \times 10^3$ pmol/min per ml respectively. In addition the medium in wells 9 to 12 and 17 to 20 was made 5 mM mannose-6-phosphate. The cells were then incubated for 6 hours after which time they were rinsed with medium and fresh medium added. The cells were incubated overnight and then harvested, washed and lysed as described above. The cell lysates were dialysed against 5 mM-sodium acetate, pH 4.0, for 16 h at 4° C. and then analysed for IDS activity and total protein.

Subcellular fractionation

Cells from SF-635 were grown to confluency in 75 $cm^2$ flasks and then exposed to medium supplemented with $5 \times 10^4$ pmol/min per ml rIDS. The cells were incubated for 72 h then harvested and fractionated on Percoll density gradients as described in Anson et al (27). The resulting gradient was collected in 1.0 ml fractions by bottom puncture and the fractions analysed for IDS and β-hexosaminidase activity.

Large-scale production of rIDS

CHOEFI2S-9 cells were inoculated into two 2-layer cell factories (NUNC, 1200 $cm^2$) in Ham's F12, 10% v/v FCS and antibiotics. Cells were grown to confluency, the medium removed and the cells were then rinsed 3-times with PBS and re-fed with 200 ml of Ham's F12 without FCS but supplemented with antibiotics and 10 mM-$NH_4Cl$. After 4 days in culture, the medium was collected and replaced with Ham's F12, 10% v/v FCS and PSK but without $NH_4Cl$ for 3 days. This cycle was repeated several times. The conditioned serum free Ham's F12 medium supplemented with $NH_4Cl$ was collected, clarified by filtration (0.2 $\mu$M filture; Millipore) and stored at 4° C.

The rIDS was purified from the collected medium by a 3-step column procedure. The medium was dialysed overnight at 4° C. against 30 mM-Tris/HCl, pH 7.0/10% v/v glycerol/0.2 mM-DTE/3 mM-$NaN_3$ (buffer A) and was applied to a PBE94 column (8 cm×1.5 cm) equilibrated in buffer A (flow-rate 1.0 ml/min) and then washed with 100 ml of buffer A. Bound proteins were diluted with polybuffer 74 that had been diltured 1:18 with water, the pH adjusted to 4.0 with HCl and the solution made 10% v/v in glycerol, 0.1 mM-DTE and 3 mM-$NaN_3$. The column was further eluted with 100 ml 15 mM-dithiothreitol/3 mM-$NaN_3$ (buffer B). The rIDS eluted in buffer B was applied at a flow-rate of 1.0 ml/min to a Blue A agarose column (6 cm×0.7 cm) also equilibrated in buffer B. The rIDS activity from this step was applied in 1.0 ml volumes to an LKB Ultrachrom GTi f.p.l.c. system with a TSK G3000SW Ultrapac column (30 cm×0.8 cm) equilibrated and eluted in buffer B at a flow-rate of 0.5 ml/min and pressure of 150 kPa. Fractions containing rIDS activity were pooled and analysed under denaturing and non-denaturing condition on SDS-PAGE (10% w/v acrylamide) to estimate apparent subunit size. Gels were stained with either Gradipure Colloidal Electrophoresis Gel Stain (Gradipure, Pyrmont, NSW) or silver stained according to the method of Merril et al (32). Native molecular mass was determined using the f.p.l.c. system as described elsewhere (3) Kinetic (Km, Vmax, pH optima) and inhibition data were obtained as previously described (3).

Endoglycosidase F treatment of IDS

To two identical 60 $\mu$l samples, each containing 2.5 ug of rIDS, was added an equal volume of buffer containing 100 mM-sodium phosphate, pH 6.1/50 mM-EDTA/1% v/v Nonidet P40/0.1% v/v SDS/1% v/v 2-mercaptoethanol. After boiling both samples for 5 min, to one was added 1 unit and to the other 5 units of endoglycosidase. Both samples were incubated for 17 h at 37° C. A control sample was untreated but stored in similar buffer conditions at 4° C. Bromophenol blue was added to each sample before analysis on SDS-PAGE. Molecular-mass standards were applied to SDS-PAGE in the same buffer as the enzyme samples.

2. RESULTS

Construction of IDS expression vectors

Figure 4:
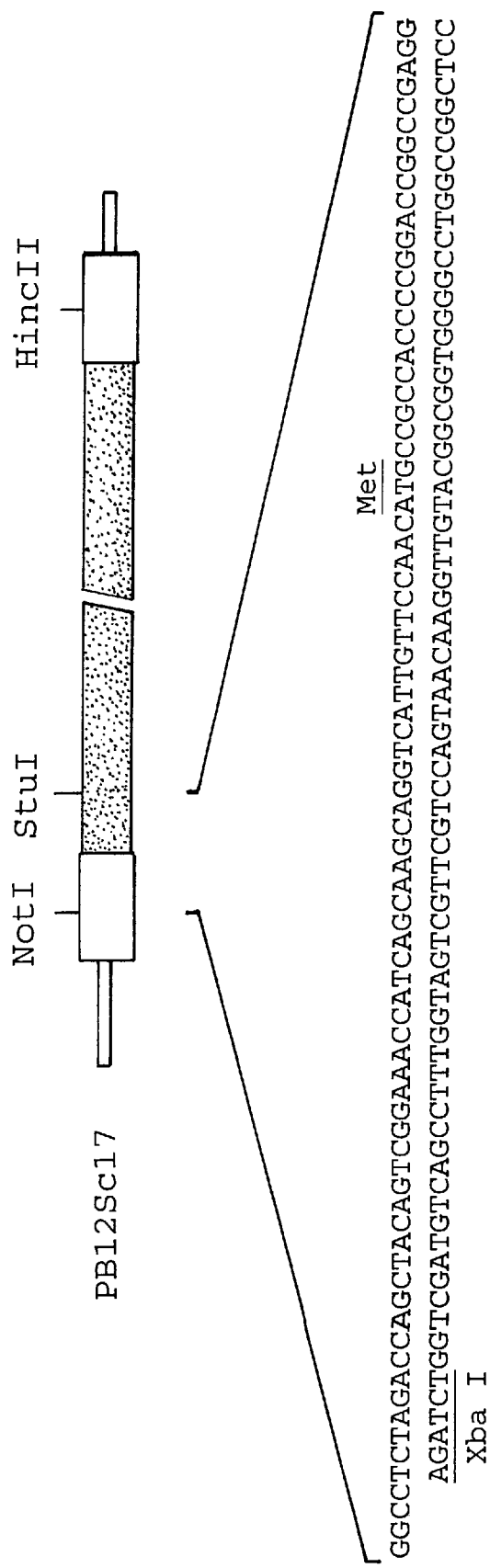
FIG. 4 is a schematic representation showing the construction of a chimeric IDS cDNA. The full length IDS cDNA clone, pB12Sc17, is shown with the unique NotI, StuI and HincII restriction enzyme sites marked. The narrow open bar indicates plasmid vector sequence, the solid bar coding sequence and the large open bar non-coding sequence. The oligonucleotide sequence inserted in place of the sequence removed by NotI/StuI digestion is shown below with the unique XbaI restriction enzyme site and the ATG (Met) initiation codon indicated.

An initial expression construct containing an IDS cDNA from pB12Sc17 cloned into pRSVN.08 expressed I2S at very low levels when introduced into CHO-K1 cells. A chimeric I2S cDNA was then made by replacing the 5' non-coding sequence of the I2S cDNA with 45 bp of the rat preproinsulin leader sequence (FIG. 4) as an analogous chimeric N-acetylgalactosamine-4-sulfatase cDNA construct resulted in the expression of high levels of enzyme activity in the same system (27). Briefly, the sequence shown in FIG. 4 was synthesised as two complementary oligonucleotides which were then kinased and annealed. The resulting double stranded fragment was then cloned between the dephosphorylated NotI and StuI sites of pB12Sc17. The resulting construct was designated pB12SNC.1. The IDS cDNA insert was then excised from pB12SNC.1 with XbaI and HincII and cloned into XbaI/EcoRV restricted and dephosphorylated pRSVN.08 resulting in the construct pRSVN.2SNC1. In order to further increase expression of rIDS the chimeric rIDS cDNA was placed under the transcriptional control of the human elongation factor-1α (EF-1α) gene promoter. This was done by excising the RSV-LTR from pRSVN.2SNC1 by SalI/XbaI digestion and inserting the HindIII/XbaI fragment from pEF-BOS (32), after making the HindIII and SalI ends blunt by filling in with the Klenow fragment of DNA polymerase I. This construct was designated pEFN.2SNC1. Both pRSVN.2SNC1 and pEFN.2SNC1 were electroporated into CHO-K1 cells and G418 resistant clonal cell lines isolated. Individual clones were assayed for secretion of IDS activity into the culture medium. Replacement of RSV-LTR promoter with EF-1α promoter resulted in a 2-fold enhancement of IDS expression. A clonal cell line, CHOEFI2S-9, was selected on the basis of maximum expression of IDS activity. This clone secreted IDS such that after 5 days of culture approximately 11 mg of IDS accumulated per liter of medium.

Large-scale production of rIDS

Conditioned serum-free Ham's F12 medium containing $NH_4Cl$ was collected as described above. Enzyme was collected in this manner to facilitate purification by minimising total protein in medium. As prolonged exposure to this medium resulted in loss of cell viability the cells were cycled in Ham's F12 with 10% v/v FCS to allow recovery. A total of 1 liter of serum free medium, containing approximately 11 mg of rIDS was collected in this matter.

Figure 5:
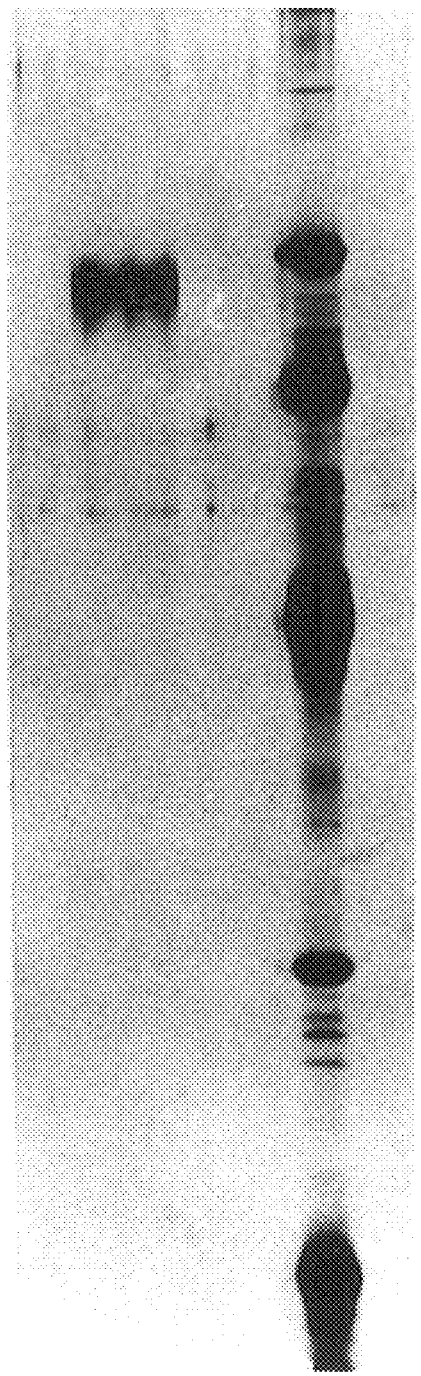
FIG. 5 is a photographic representation of SDS/PAGE of recombinant (r) IDS. rIDS (lane 1) and molecular mass standards (lane 2) were reduced with DTE and electrophoresed as detailed in Example 2 and then Silver stained. The sizes of the molecular mass standards are indicated on the right of the figure and the estimated mass of the rIDS on the left. All masses are in kDa.

The rIDS bound very tightly to PBE94 medium and not not eluted in significant amount during polybuffer elution (less than 10% of the total enzyme recovered from this column was eluted with polybuffer, pool A). The majority of rIDS (pool B) had a pI of <4.0 and required NaCl for elution. Enzyme was eluted in buffer B in concentrated from (essentially in one 10 ml fraction). This permitted direct application to Blue A agarose. Although the rIDS did not bind to this matrix it was a necessary step to remove some minor contaminating proteins which were observed after f.p.l.c. when the enzyme from the chromatofocusing step was applied directly to f.p.l.c. Recovery of activity from Blue A agarose was 80%. The final step in the purification (f.p.l.c.) resulted in overall recovery of greater than 15% activity. The estimated native molecular mass on f.p.l.c. was 90 kDa. A single diffuse protein band of 80–92 kDa was observed when a sample from the f.p.l.c. step was subjected to SDS-PAGE (FIG. 5). This diffuse band was observed on SDS-PAGE run under reducing or non-reducing conditions indicative of a single subunit species with no disulphide bonding. Correlation of the protein species observed as a diffuse band on SDS-PAGE with IDS activity was demonstrated by PAGE run under non-reducing conditions, according to the method of Laemmli (33), but with the modification that SDS was omitted from all buffers. Identical amounts of enzyme were applied to 2 lanes of the gel. One lane was stained for protein and as with SDS-PAGE a single diffuse band was observed. The other was cut into 2 mm slices and each slice was incubated in 4-times the volume of assay mix at 37° C. overnight. When corrected for swelling which occurred during the staining procedure, the position of the diffuse band corresponded to that of IDS activity in the lane that was sliced and assayed.

Figure 6:
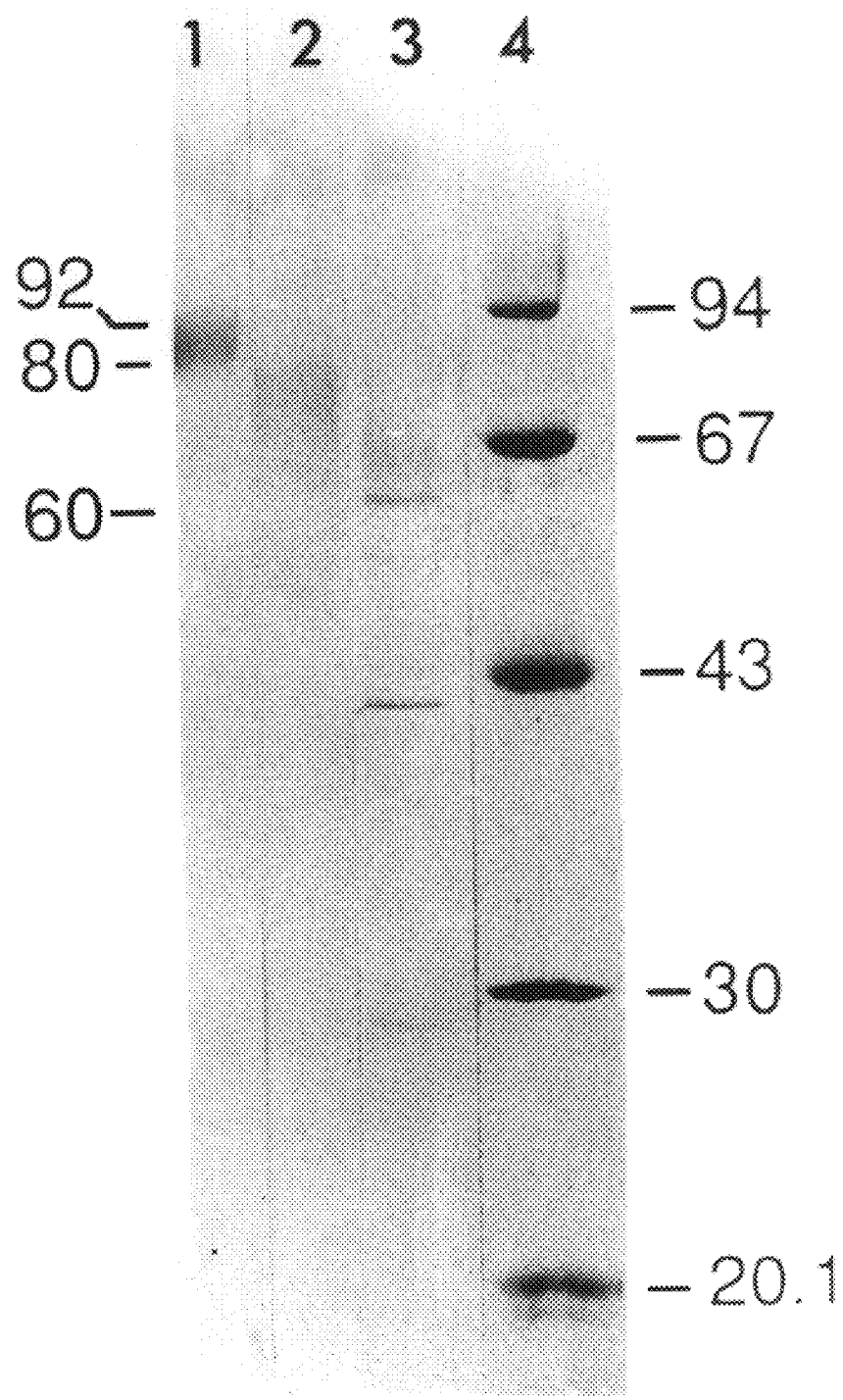
FIG. 6 is a photographic representation showing SDS/PAGE of rIDS after treatment with endoglycosidase F. rIDS was treated with endoglycosidase F, reduced, electrophoresed and stained with Gradipure Colloidal Gel Stain. Lane 1 contains untreated rIDS and lanes 2 and 3 rIDS treated with 1 and 5 units of endoglycosidase F, respectively. Lane 4 contains molecular mass standards with the sizes, in kDa, indicated to the right of the figure.

The molecular size of IDS (after cleavage of the signal peptide) estimated from cDNA sequence data indicated a maximum of 58 kDa with 7 potential glycosylation sites (see Example 1). The mature or processed forms of IDS had various molecular sizes depending on the column matrix used. The native molecular size varied from 42 kDa to 65 kDa while, on a denaturing SDS-PAGE, two polypeptide bands of 43 kDa and 14.4 kDa were consistently observed. The recombinant form of IDS had a markedly larger molecular size (80–90 kDa; FIG. 5) than predicted. The diffuse nature of the Coomassie-stained band on SDS-PAGE implied that the protein was highly and variably glycosylated. To test the hypothesis that the difference in the observed Mr and the expected estimated value was due to carbohydrate, rIDS was treated with endoglycosidase F as outlined above. Treatment with 1 unit of endoglycosidase F resulted in a decrease in Mr (70 kDa–80 kDa). However, the enzyme still migrated as a diffuse band on SDS-PAGE (FIG. 6, lane 1). Lane 2, which shows the result of treatment with 5-times the concentration of endoglyosidase F, demonstrates the presence of a tightly staining 60 kDa protein band with a diffuse band above it (62 kDa to 68 kDa). Other bands are due to endoglycosidase F.

These data suggest that the 60 kDa band is the end product of the deglycosylation of rIDS by endoglycosidase F and that the diffuse bands in both lanes are the result of incomplete digestion. Endoglycosidase F cleaves the glycosidic bond between GlcNAc residues of the chitobiose core in the N-linked carbohydrate chains resulting in one GlcNAc residue remaining linked to asparagine. This would account for approximately 1540 kDa due to carbohydrate if all 7 of the glycosylation sites were utilised and may therefore account for the molecular size of IDS after endoglycosidase F treatment as being 60 kDa rather than 58 kDa.

Kinetics of rIDS

Although both the liver and rIDS show a similar Km towards the disaccharide substrate (IdoA2S-anM6S) in the standard assay (50 mM sodium acetate pH 4.5 and 500 µg/ml BSA) they have a substantially different Vmax. This suggests that the recombinant form of the enzyme may be less efficient in turning over the substrate than the mature form. Alternatively, this may reflect a difference between enzyme produced in CHO cells and in liver. Both the (CHO) recombinant and (liver) mature form of the enzyme have similar pH optima and specific activities (Table 2).

Inhibition studies showed that the rIDS was similar to the liver enzyme with regard to inhibition by sulphate, phosphate and copper ions. The rIDS appears to be less sensitive to salt inhibition than liver enzyme (Table 3).

Demonstration of correction of MPS II fibroblasts

Fibroblasts from patients with MPS II store undergraded HS and DS fragments. This storage is reflected in the accumulation of labelled material when the cells are metabolically labelled with $Na_2^{35}SO_4$. Supplementing culture medium with rIDS at $5 \times 10^4$ pmol/min per ml resulted in clearance of this stored product to levels comparable to those seen in control fibroblasts (Table 4) and to levels of IDS activity 40- to 80-fold above normal in SF1779 and SF635 respectively. The activity of a second lysosomal enzyme, β-hexosaminidase, was not affected by endocytosis of IDS (Table 4).

To test whether endocytosis of the rIDS occurs via the mannose-6-phosphate receptor MPS II cells (SF-1779) were cultured in medium supplemented with rIDS at $5 \times 10^4$ and $5 \times 10^3$ pmol/min per ml in the presence or absence of 5 mM mannose-6-phosphate. Inhibition of the uptake of IDS activity by mannose-6-phosphate at both doses of enzyme confirmed that uptake is mediated via the mannose-6-phosphate receptor.

Localisation of endocytosed rIDS

Endocytosed rIDS was instrumental in correcting the lysosomal storage in MPS II skin fibroblasts, as demonstrated by the loss of accumulated $S^{35}$-labelled material. Confirmation of the subcellular localisation of the endocytosed enzyme was demonstrated by fractionating the postnuclear supernatant of corrected and control MPSII skin fibroblasts on Percoll gradients as described above. Analysis of these gradients showed that in the corrected MPS II cells, IDS activity fractionated with the lysosomal enzyme β-hexosaminidase in the dense fraction of the gradient. Control MPS II fibroblasts contained no detectable levels of IDS activity and a similar β-hexosaminidase activity profile.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 2

Comparison of the Catalytic Properties of Recombinant and Liver IDS

|  | Km (µM) | Vmax (µmol/min per mg) | Specific Activity (µmol/min per mg) | pH Optimum |
|---|---|---|---|---|
| Liver IDS | 4.0 | 80 | 11.9 | 4.5 |
| rIDS | 3.0 | 3.35 | 20.8 | 4.5 |

TABLE 3

Comparison of the Effect of Various Inhibitors on Recombinant and Liver IDS

|  | NaCl (mM) | $Na_2SO_4$ (µM) | $Na_2HPO_4$ (µM) | Cu Acetate (mM) |
|---|---|---|---|---|
| Liver IDS | 40 | 50 | 30 | 15 |
| rIDS | 160 | 115 | 35 | 8 |

Values shown are for 50% inhibition of IDS activity. For details, see Materials and Methods section.

TABLE 4

Correction of the MPS II Defect by Recombinant IDS

| | IDS (pmol/min per mg) | | β-Hexosaminidase (nmol/min per mg) | | $^{35}$S-cpm/mg Cell Protein | |
|---|---|---|---|---|---|---|
| SF-3409 | 13.5 ± 2.2 | (n = 3) | 83.0 ± 7.8 | (n = 3) | 3138 ± 491 | (n = 3) |
| SF-1779 | n.d. | (n = 3) | 150 ± 10 | (n = 3) | 196927 ± 21247 | (n = 3) |
| SF-1779 + rISD | 562 ± 99 | (n = 3) | 118 ± 11 | (n = 3) | 5136 ± 502 | (n = 3) |
| SF-635 | 1.6 ± 1.5 | (n = 3) | 269 ± 29 | (n = 3) | 233080 ± 66010 | (n = 3) |
| SF-635 ± rISD | 1140 ± 50 | (n = 3) | 257 ± 14 | (n = 3) | 9018 ± 1988 | (n = 3) | n = number of experimental repeats;
n.d. = none detected
Normal and MPS II fibroblasts were labelled with Na$_2^{35}$SO$_4$ and exposed to 5 × 10$^4$ pmol/min per ml of rIDS as described in Materials and Methods. Undialysed cell lysates were analysed for IDS activity, total protein, β-hexosaminidase activity and radioactivity.

REFERENCES

1. Neufeld, E. F. & Muenzer, J. (1989) in *The Metabolic Basis of Inherited Disease,* eds. Scriver, C. R., Beaudet, A. L., Sly, W. S. & Valle, D. (McGraw-Hill, New York), pp. 1565–1587.

2. Shapiro, L. J. (1989) in *The Metabolic Basis of Inherited Disease,* eds. Scriver, C. R., Beaudet, A. L., Sly, W. S. & Valle, D. (McGraw-Hill, New York), pp. 1945–1964.

3. Bielicki, J., Freeman, C., Clements, P. R. & Hopwood, J. J. (1990) *Biochem, J.,* 271: 75–86.

4. Matsudaira, P., (1987) *J. Biol. Chem.* 262: 10035–10038.

5. Sanger, R., Nicklen, S., & Coulson, A. R. (1977) *Proc. Natl. Acad. Sci.* USA 74: 5463–5467.

6. Nelson, P. V., Carey, W. F., Morris, C. P., & Pollard, A. C. (1989) *Med. J. Aust.* 151: 126–131.

7. Chomczynski, P. & Sacchi, N. (1987) *Anal. Biochem.* 162: 156–159.

8. Reisner, A. H., & Bucholtz, C. (1987) *Nature* (London) 314: 310.

9. Lipman, D. J., Altschul, S. F. & Kececioglu, J. D. (1989) *Proc. Natl. Acad. Sci.* USA 86: 4412–4415.

10. Masuyama, T., Gojobori, T., Aota, S. & Ilkemura, T. (1986) *Nucleic Acids Res.* 14: r151–t197.

11. Kozak, M. (1987) *Nucleic Acids Res.* 15: 8125–8131.

12. von Heijne, G. (1986) *Nucleic Acids Res.* 14: 4683–4690.

13. Hasilik, A. & von Figura, K. (1984) in *Lysosomes in Biology and Pathology*eds. Dingle, J. T. & Sly, W. S. (Elsevier, Amsterdam) Vol. 7, pp. 3–16.

14. Stein, C., Gieselmann, V., Kreysing, J., Schmidt, B., Pohlmann, R., Waheed, A., Meyer, H. E., O'Brien, J. S. & von Figura, K. (1990) *J. Biol. Chem.* 265: 3374–3381.

15. Peters, C., Schmidt, B., Rommerskirch, W., Rupp, K., Zuhlsdorf, M., Vingron, M., Meyer, H. E., Pohlmann, R. & von Figura K. (1990) *J. Biol. Chem.* 265: 3374–3381.

16. Yen, P. H., Marsh, B., Allen, E., Tsai, S. P., Ellison, J., Connolly, L., Neiswanger, K. & Shapiro, L. J. (1988) *Cell* 55: 1123–1135.

17. Oshima, A., Kyle, J. W., Miller, R. D., Hoffman, J. W., Powell, P., Grubb, J. H., Sly, W. S., Tropak, M., Guise, S. & Gravel, R. A. (1987) *Proc. Natl. Acad. Sci.* USA 84: 685–689.

18. Morreau, H., Galjart, M. J., Gillemands, N., Willemsen, R., van Horst, T. J. & d'Azzo, A. (1989) *J. Biol. Chem.* 264: 20655–20663.

19. Robertson, D. A., Freeman, C., Nelson, P. V., Morris, C. P. & Hopwood, J. J. (1988) *Biochem. Biophys. Res. Commun.* 157: 218–224.

20. Yen, P. H., Allen, E., Marsh, B., Mohandas, T., Wang, N., Taggart, R. T. & Shaapiro, L. J. (1987) *Cell* 49: 443–454.

21. Stein, C., Hille, A., Seidel, J., Rijnbout, S., Waheed, A., Schmidt, B., Geuze, H & von Figura, K. (1989) *J. Biol. Chem.* 254: 13865–13872.

22. Sasaki, H., Yamada, K., Akasaka, K., Kawasaki, H., Suzuki, K., Saito, A., Sato, M. & Shimada, H. (1988) *Eur. J. Biochem.* 177: 9–13.

23. Dayhoff, M. O., Schwartz, R. M. & Orcatt, B. C. (1978) in *Atlas of Protein Sequence and Structure,* ed. Dayhoff, M. O. (Natl. Biomed. Res. Found, Washington, DC) Vol. 5, Suppl. 3, pp. 345–352.

24. Lee, G. D. & van Etten, R. L. (1975) *Arch. Biochem. Biophys.* 171: 424–434.

25. James, G. T. (1979) *Arch. Biochem. Biophys.* 197: 57–62.

26. Ausubel, F. M., Brent, R., Kingston, R. E., Moore, D. D., Seidman, J. G., Smith, J. A. and Struhl, K. (1989) *Current Protocols in Molecular Biology,* Wiley Interscience, New York.

27. Anson, D. S., Taylor, J. A., Bielicki, J., Harper, G. S., Peters, C., Gibson, G. J. and Hopwood, J. J. (1992) *Biochem. J.* 284: 789–794.

28. Hopwood, J. J., Muller, V., Harrison, J. R., Carey, W. F., Elliott, H., Robertson, E. F. and Pollard, A. C. (1982) *Med. J. Aust.* 1: 257–260.

29. Lowry, O. H., Rosebrough, N. H. Farr, A. L. and Randell, R. J. (1951) *J. Biol. Chem.* 193: 265–275.

30. Leaback, D. H. and Walker, P. G. (1961) *Biochem. J.* 78: 151–156.

31. Merril, C. R. Goldman, D., Sedman, S. A. and Ebert, M. H. (1981) *Science* 211: 1437–1438.

32. Mizushima, S. and Nagata, S. (1990) *Nuc. Acids. Res.* 18: 5322.

33. Laemmli, U. K. (1970) *Nature* (London) 227: 680–685.

What is claimed is:

1. A recombinant human iduronate 2-sulfatase (IDS) wherein said recombinant IDS is more highly glycosylated than the naturally occurring enzyme isolated from human tissue and wherein said recombinant human IDS is produced in Chinese Hamster Ovary (CHO) cells.

2. The recombinant IDS according to claim 1 having a molecular weight in the range of from about 70 k Da to about 90 kDa as determined using SDS/PAGE.

3. A pharmaceutical composition useful for treating patients suffering from a deficiency in iduronate 2-sulfatase (IDS) comprising one or more pharmaceutically acceptable carriers or diluents and a recombinant human IDS wherein said recombinant human IDS is produced in Chinese Hamster Ovary (CHO) cells and is more highly glycosylated than the naturally occurring enzyme isolated from human tissue.

4. The pharmaceutical composition of claim 3 wherein said recombinant human IDS produced in Chinese Hamster Ovary (CHO) cells has a molecular weight in the range of from about 70 k Da to about 90 kDa as determined using SDS/PAGE.

5. A recombinant human iduronate 2-sulfatase (IDS) having the sequence of SEQ ID NO:2 produced in Chinese Hamster Ovary (CHO) cells wherein said recombinant IDS has a longer half-life than native IDS produced by human liver cells.

6. A recombinant human iduronate 2-sulfatase (IDS) having the sequence of SEQ ID NO:2 produced in Chinese Hamster Ovary (CHO) cells wherein said recombinant IDS is taken up by mucopolysaccharidosis cells to a greater degree than native IDS produced by human liver cells.

7. A recombinant human iduronate 2-sulfatase (IDS) which is more highly glycosylated than IDS isolated from human tissue and wherein said recombinant IDS comprises a fusion protein.

8. The recombinant IDS of claim 7 wherein the fusion protein comprises a proteinaceous molecular selected from the group consisting of an enzyme, a reporter molecule, a purification moiety, and an amino acid.

9. A recombinant human iduronate 2-sulfatase (IDS) wherein said IDS is produced in a human cell and wherein said IDS is more highly glycosylated than IDS isolated from human tissue.

10. A recombinant human iduronate 2-sulfatase (IDS) according to claim 9 wherein said human cell is a fibroblast.

11. A recombinant human iduronate 2-sulfatase (IDS) of claim 10 wherein the fibroblast is a human diploid fibroblast.

12. A recombinant human iduronate 2-sulfatase (IDS) of claim 10 wherein the fibroblast is from a human fibroblast cell line.

13. A recombinant human iduronate 2-sulfatase (IDS) of claim 12 wherein the human fibroblast cell line is SF-635, SF-1779, or SF-3409.

14. A pharmaceutical composition useful for treating patients suffering from a deficiency of iduronate 2-sulfatase (IDS), said composition comprising one or more pharmaceutically acceptable carriers or diluents and a recombinant IDS wherein said recombinant IDS is more highly glycosylated than IDS isolated from human tissue.

15. The pharmaceutical composition of claim 14 wherein said recombinant iduronate 2-sulfatase (IDS) is produced in a eukaryotic cell.

16. The pharmaceutical composition of claim 15 wherein the eukaryotic cell is a fibroblast or Chinese Hamster Ovary (CHO) cell.

17. The pharmaceutical composition of claim 16 wherein the fibroblast is a human diploid fibroblast.

18. The pharmaceutical composition of claim 16 wherein the fibroblast is from a human fibroblast cell line.

19. The pharmaceutical composition of claim 18 wherein the human fibroblast cell line is SF-635, SF-1779, or SF-3409.

* * * * *